US012241130B2

(12) United States Patent
Henderson et al.

(10) Patent No.: US 12,241,130 B2
(45) Date of Patent: Mar. 4, 2025

(54) DETECTION OF INFECTIOUS AGENTS FROM ENVIRONMENTAL AIR DUST

(71) Applicant: Charles River Laboratories International, Inc.

(72) Inventors: Kenneth S. Henderson, Wilmington, MA (US); John M. Coiro, Princeton, NJ (US); Brian M. Bilecki, Medford, NJ (US); Thomas P. Schupsky, Cream Ridge, NJ (US)

(73) Assignee: CHARLES RIVER LABORATORIES INTERNATIONAL, INC., Wilmington, MA (US)

( * ) Notice: Subject to any disclaimer, the term of this patent is extended or adjusted under 35 U.S.C. 154(b) by 813 days.

(21) Appl. No.: 17/193,597

(22) Filed: Mar. 5, 2021

(65) Prior Publication Data

US 2021/0189510 A1 Jun. 24, 2021

Related U.S. Application Data

(63) Continuation of application No. 15/170,660, filed on Jun. 1, 2016, now Pat. No. 10,954,573.
(Continued)

(51) Int. Cl.
*C12Q 1/6888* (2018.01)
*A01K 1/03* (2006.01)
(Continued)

(52) U.S. Cl.
CPC ............ *C12Q 1/6888* (2013.01); *A01K 1/031* (2013.01); *C12Q 1/6806* (2013.01); *C12Q 1/689* (2013.01);
(Continued)

(58) Field of Classification Search
CPC .... C12Q 1/6888; C12Q 1/6806; C12Q 1/689; C12Q 1/6893; A01K 1/031; G01N 1/2205; G01N 1/2247; G01N 1/2273
(Continued)

(56) References Cited

U.S. PATENT DOCUMENTS 4,343,261 A * 8/1982 Thomas ................. A01K 1/031
119/418
5,749,321 A * 5/1998 Ikuse ..................... A01K 1/031
119/458
(Continued)

FOREIGN PATENT DOCUMENTS

CN 104056492 A 9/2014
CN 104689654 A 6/2015
(Continued)

OTHER PUBLICATIONS

Brena Mauck, Cholinesterase inhibitors and stress: Effects on brain muscarinic receptor density in mice, NeuroToxicology, vol. 31, Issue 5, 2010,(https://www.sciencedirect.com/science/article/pii/S0161813X1000121X) Jun. 11, 2010 (Year: 2010).*
(Continued)

*Primary Examiner* — Xin Y Zhong
*Assistant Examiner* — Monica S Young
(74) *Attorney, Agent, or Firm* — MEDLER FERRO WOODHOUSE & MILLS PLLC

(57) ABSTRACT

Embodiments of the present disclosure are directed to systems and methods for collection and analysis of environmental air dust (EAD) within an individually ventilated cage rack (IVR) environment for detecting pathogens. The method includes collection of an EAD sample by a collection media, isolation of a plurality of nucleic acids (e.g., RNA and/or DNA) representative of one or more infectious agents from the EAD sample, optional reverse transcription
(Continued)

of RNA to cDNA if the isolated nucleic acids contain RNA, amplification of the cDNA and/or DNA (e.g., by polymerase chain reaction (PCR)), and assay interpretation. Optionally, the EAD sample may be analyzed with one or more other sample types (e.g., fecal pellets, oral swabs, body swabs, tissue, etc.) to improve detection of low-copy organisms.

37 Claims, 16 Drawing Sheets

Related U.S. Application Data

(60) Provisional application No. 62/280,057, filed on Jan. 18, 2016, provisional application No. 62/169,438, filed on Jun. 1, 2015.

(51) Int. Cl.
    *C12Q 1/6806*     (2018.01)
    *C12Q 1/689*      (2018.01)
    *C12Q 1/6893*     (2018.01)
    *G01N 1/22*       (2006.01)

(52) U.S. Cl.
    CPC ......... *C12Q 1/6893* (2013.01); *G01N 1/2205* (2013.01); *G01N 1/2247* (2013.01); *G01N 1/2273* (2013.01)

(58) Field of Classification Search
    USPC ........................................................ 73/28.01
    See application file for complete search history.

(56) References Cited

U.S. PATENT DOCUMENTS

| | | | | |
|---|---|---|---|---|
| 5,778,822 | A * | 7/1998 | Giffin | A01K 1/0047 119/500 |
| 5,996,535 | A * | 12/1999 | Semenuk | A01K 1/031 119/493 |
| 6,156,089 | A | 12/2000 | Stemmer et al. | |
| 6,257,171 | B1 * | 7/2001 | Rivard | A01K 1/031 119/419 |
| 6,394,033 | B1 * | 5/2002 | Trogstam | A01K 1/031 119/419 |
| 6,571,738 | B2 | 6/2003 | Rivard | |
| 6,782,845 | B1 * | 8/2004 | Schmidt | A01K 1/0047 119/419 |
| 6,932,850 | B1 | 8/2005 | Welch et al. | |
| 8,211,951 | B2 | 7/2012 | Lloyd et al. | |
| 8,936,176 | B2 | 1/2015 | Roe | |
| 2003/0192485 | A1 * | 10/2003 | Opfel | A01K 1/0107 119/526 |
| 2003/0192816 | A1 * | 10/2003 | Opfel | A01K 1/0107 209/133 |
| 2009/0095697 | A1 * | 4/2009 | Gabriel | A01K 1/031 211/206 |
| 2011/0005465 | A1 * | 1/2011 | Tamborini | A01K 1/0047 119/419 |
| 2011/0041773 | A1 | 2/2011 | Brielmeier et al. | |
| 2012/0045752 | A1 | 2/2012 | Ensor et al. | |
| 2013/0068098 | A1 * | 3/2013 | Haslam | B01D 46/10 55/385.2 |
| 2013/0157870 | A1 | 6/2013 | Pushkarev et al. | |
| 2014/0165832 | A1 * | 6/2014 | Antoun | B01D 45/04 55/438 |
| 2015/0004679 | A1 * | 1/2015 | Conger | A01K 1/031 435/287.2 |
| 2015/0209708 | A1 * | 7/2015 | Ordakowski | B01D 46/0002 55/501 |
| 2016/0348186 | A1 * | 12/2016 | Henderson | A01K 1/0058 |
| 2017/0254827 | A1 * | 9/2017 | Walker | G01N 35/04 |

FOREIGN PATENT DOCUMENTS

| | | |
|---|---|---|
| WO | WO 2005/017181 A2 | 2/2005 |
| WO | WO 2007/083147 A2 | 7/2007 |
| WO | WO 2014/018265 A2 | 1/2014 |

OTHER PUBLICATIONS

Abstracts of Scientific Presentations, 2016 AALAS National Meeting, Charlotte, North Carolina, Journal of the American Association for Laboratory Animal Science, 55(5):606-710, retrieved on Jun. 18, 2019 from https://www.aalas.org/national-meeting/abstract-archive.

Burton et al., "Physical Collection Efficiency of Filter Materials for Bacteria and Viruses", *Annals of Occupational Hygiene* 2007; 51:143-151.

Compton et al., "Efficacy of Three Microbiological Monitoring Methods in a Ventilated Cage Rack", *Comparative Medicine* 2004; 54:382-392.

Compton et al., "Effect of Cage-Wash Temperature on the Removal of Infectious Agents from Caging and the Detection of Infectious Agents on the Filters of Animal Bedding-Disposal Cabinets", *Journal of the American Association for Laboratory Animal Science* 2015; 54:745-755.

European Office Action issued for European Patent Application No. 16730597.8, dated Dec. 18, 2018 (4 pages).

Henderson et al., "Efficacy of Direct Detection of Pathogens in Naturally Infected Mice by Using a High-Density PCR Array", *Journal of the American Association for Laboratory Animal Science* 2013; 52(6):763-772.

Henderson et al., "Environmental Monitoring for the Presence of Rodent Parvoviruses on Room Air Intake Filters via the Polymerase Chain Reaction (PCR)", *Laboratory Animal Science*, 1998; 48, 22 pp. (PowerPoint version of lecture presented at the 1998 National AALAS conference).

Henderson et al., "Environmental Monitoring for the Presence of Rodent Parvoviruses on Room Air Intake Filters via the Polymerase Chain Reaction (PCR)," Contemporary Topics by the American Association for Laboratory Animal Science 1998; 37(4):88 (Abstract).

Henderson et al., "A Guide to Integrating PCR Rodent Infectious Agent (PRIA) Panels in Rodent Quality Control Programs", Charles River Laboratories International Inc., 2013.

International Search Report with Written Opinion corresponding to International Patent Application No. PCT/US2016/035311, mailed Aug. 30, 2016.

Jensen, "PCR Testing of a Ventilated Caging System to Detect Murine Fur Mites", *Journal of the American Association for Laboratory Animal Science* 2013; 52(1):28-33.

Jurinke et al., "MALDI-TOF Mass Spectrometry", *Molecular Biotechnology* 2004; 26:147-163.

Mackay, "Real-time PCR in the microbiology laboratory", *Clinical Microbiology and Infection* 2004; 10:190-212.

Mailhiot et al., "Comparing Mouse Health Monitoring Between Soiled-bedding Sentinel and Exhaust Air Dust Surveillance Programs", *Journal of the American Association for Laboratory Animal Science* 2020; 59:58-66.

Nakao et al., "Mitochondrial genetic code in cestodes", *Molecular and Biochemical Parasitology* 2000; 111:415-424.

Oyanagi et al., "Detection of MHV-RNAs in Mouse Intestines and in Filter Dust in Mouse Room Ventilation Duct by a Modified RT-Nested PCR", *Experimental Animals* 2004; 53:37-41.

Phaneuf et al., "Validation of Exhaust Air Dust Testing Using a Prototype Plenum Attachment and Interceptor in an IVC System with Centralized Ventilation", The Center for Phenogenomics Poster (2017).

Di Pinto et al., "A comparison of DNA extraction methods for food analysis", Food Control 18(1):76-80 (2007).

Monts De Oca et al., "Evaluation of Exhaust Air Dust PCR Testing of the Bedding Sentinel Cage Filter", Charles River, Research Models, Houston, TX, Animal Care Operations, University of Houston, TX Poster, No Date.

(56) References Cited

OTHER PUBLICATIONS

National Research Counsel, "Guide for the Care and Use of Laboratory Animals", Eighth Edition, Washington D.C., National Academic Press (2011).
Lab Products, Inc., "AllerZone," Web Page, accessed through WayBack Machine. https://labproductsinc.com/product/allerzone/ (Year: 2014).

\* cited by examiner

DETECTION OF INFECTIOUS AGENTS FROM ENVIRONMENTAL AIR DUST

CROSS-REFERENCE TO RELATED APPLICATIONS

This application is a continuation of U.S. patent application Ser. No. 15/170,660, filed Jun. 1, 2016, which application claims the benefit of U.S. Provisional Application No. 62/169,438, filed on Jun. 1, 2015, entitled "In-Line Airflow Filtration For Detection Of Infectious Agents" and U.S. Provisional Application No. 62/280,057, filed on Jan. 18, 2016, and entitled "Method And System For Monitoring Air Flow Impurity." The entire teachings of each of the above applications are incorporated herein by reference.

BACKGROUND

A requirement in biomedical research is that animals under study, typically mice, are monitored to confirm that they are free from infection with specific pathogens. In one example, pathogens can interfere with research by modulating experimental responses and contaminating biologics, even if they rarely produce disease. In another example, monitoring is needed to prepare current health reports to facilitate shipment to and from collaborating institutions. In a further example, institutional and/or governing bodies often require that periodic monitoring be performed.

In order to eliminate and then exclude pathogens, study animals are typically re-derived or cured of infection and housed behind room- or cage-level barriers, respectively. These micro-isolation cage systems have been widely adopted for maintaining and quarantining animals such as mice and rats because the cage-level barrier they provide has proven to be very effective at excluding and impeding the spread of adventitious agents. No barrier can be guaranteed 100% effective, however. Thus, routine health monitoring (HM) is still necessary in micro-isolation environments to verify the specific pathogen free (SPF) status of breeding and research colonies and imported animals in quarantine.

As study animals (e.g., rodents from research colonies) are rarely made available to be bled or euthanized for conventional HM, they are typically monitored indirectly through the use of soiled bedding sentinels (SBS). Using a soiled bedding approach, sentinel animals are housed in a plurality of cages separate from the study animals and regular changes of soiled bedding pooled from the cages of study animals are supplied to the sentinel cages. Over time, it is expected that infectious agents carried by the study animals are transferred to the pooled bedding and then to the sentinel animals. Thus, periodic screening of the soiled bedding sentinels (e.g., pathology, parasitology, bacteriology, serology, etc.) provides indirect monitoring of the health of the study animals.

Reliance on soiled bedding sentinels for routine health monitoring has been called into question in recent years, however. It is recognized that the switch to micro-isolator cages has been beneficial for limiting the transmission of pathogens but presents a poor environment for diagnostic monitoring. Notably, many agents are transmitted inefficiently, or not at all, to sentinel animals from study animals via soiled bedding. Thus, as the prevalence of infection is lowered within the micro-isolator caging, the greater the risk that the pathogen dose in pooled bedding will be insufficient to infect sentinel animals.

For at least these reasons, there exists a continued need for new systems and methods for monitoring study animals in micro-isolator cage environments.

SUMMARY

In an embodiment, a method for detecting pathogens is provided. The method includes receiving a test sample including environmental air dust captured from airflow within an exhaust plenum of an individually ventilated cage rack (IVR) by a collection media, where a surface of the collection media is oriented at an acute angle with respect to a direction of airflow within the exhaust plenum during capture of the dust sample. The method further includes isolating a plurality of nucleic acids from the test sample, where the plurality of nucleic acids is representative of one or more pathogens, amplifying at least one of the plurality of nucleic acids, and analyzing the amplified nucleic acids to identify the presence or absence of a pathogen.

In further embodiments, the method includes one or more of the following, in any combination.

In an embodiment of the method, amplifying at least one of the plurality of nucleic acids includes at least one of loop mediated isothermic amplification and polymerase chain reaction (PCR).

In an embodiment of the method, amplifying at least one of the plurality of nucleic acids includes PCR selected from the group consisting of endpoint PCR and real-time PCR.

In an embodiment of the method, isolating the plurality of nucleic acids includes extracting an RNA sample from the test sample and reverse transcribing the extracted RNA sample into a cDNA sample, amplifying at least one of the plurality of nucleic acids includes amplifying the cDNA sample by real-time PCR, and analyzing the amplified nucleic acids includes measuring a Ct value of the amplified cDNA sample.

In an embodiment of the method, isolating the plurality of nucleic acids includes extracting a DNA sample from the test sample, amplifying at least one of the plurality of nucleic acids includes amplifying the DNA sample by real-time PCR, and analyzing the amplified nucleic acids includes measuring a Ct value of the amplified DNA sample.

In an embodiment of the method, amplifying at least one of the plurality of nucleic acids includes PCR and analyzing the amplified nucleic acids includes time of flight analysis of PCR products.

In an embodiment of the method, the test sample includes environmental air dust captured from the airflow over a time period of at least 2 weeks.

In an embodiment of the method, the IVR further includes at least one cage housing a test animal.

In an embodiment of the method, the test sample further includes at least one of fecal pellets obtained from the test animal, biological material obtained from an oral swab of the test animal, biological material obtain from a body swab of the test animal, and tissue from the test animal.

In an embodiment of the method, the one or more pathogens is selected from the group consisting of: *Staphylococcus* spp., *Pasteurella* spp., *Proteus* spp., *Klebsiella* spp., *Giardia* spp., *Cryptosporidium* spp., *Entamoeba* spp., *Spironucleus* spp., Murine norovirus, *Pseudomonas* spp., and beta-hemolytic *Streptococcus* spp.

In an embodiment of the method, isolating the plurality of nucleic acids includes at least one of magnetic isolation, column-based nucleic acid isolation, organic extraction methods, and alkaline lysis.

In an embodiment of the method, the IVR does not include a cage housing a sentinel animal.

In an embodiment of the method, the collection media includes a filter selected from the group consisting of mechanical filters, chemical filters, electrostatic filters, and wet scrubbers.

In an embodiment of the method, the collection media possesses an efficiency selected within the range between 5% to 40%.

In an embodiment of the method, the collection media is a graded filter.

In an embodiment of the method, the angle of the collection media during capture of the dust sample is selected from the range of 15° to 25° with respect to the direction of airflow within the exhaust plenum.

In another embodiment, a method for detecting pathogens is provided. The method includes receiving a test sample including environmental air dust captured from airflow passing through an enclosure by a collection media, the enclosure including a chamber containing an animal cage in fluid communication with the airflow and the environmental air dust released by agitation of soiled bedding of a test animal positioned within the animal cage. The method further includes isolating a plurality of nucleic acids from the test sample, where the plurality of nucleic acids is representative of one or more pathogens, amplifying at least one of the plurality of nucleic acids, and analyzing the amplified nucleic acids to identify the presence or absence of a pathogen.

Further embodiments of the method may include one or more of the following, in any combination.

In an embodiment of the method, amplifying at least one of the plurality of nucleic acids includes at least one of loop mediated isothermic amplification and polymerase chain reaction (PCR).

In an embodiment of the method, amplifying at least one of the plurality of nucleic acids includes PCR selected from the group consisting of endpoint PCR and real-time PCR.

In an embodiment of the method, isolating the plurality of nucleic acids includes extracting an RNA sample from the test sample and reverse transcribing the extracted RNA sample into a cDNA sample, amplifying at least one of the plurality of nucleic acids includes amplifying the cDNA sample by real-time PCR, and analyzing the amplified nucleic acids includes measuring a Ct value of the amplified cDNA sample.

In an embodiment of the method, isolating the plurality of nucleic acids includes extracting a DNA sample from the test sample, amplifying at least one of the plurality of nucleic acids includes amplifying the DNA sample by real-time PCR, and analyzing the amplified nucleic acids includes measuring a Ct value of the amplified DNA sample.

In an embodiment of the method, amplifying at least one of the plurality of nucleic acids includes PCR and analyzing the amplified nucleic acids includes time of flight analysis of PCR products.

In an embodiment of the method, the test sample includes environmental air dust captured from the airflow over a time period of at least 2 weeks.

In an embodiment of the method, the environmental air dust is released by agitation of the soiled bedding by a test animal.

In an embodiment of the method, the environmental air dust is released by an actuation device in mechanical communication with the enclosure.

In an embodiment of the method, the enclosure does not contain an animal during capture of the environmental air dust.

In an embodiment of the method, the test sample further includes at least one of fecal pellets obtained from the test animal, biological material obtained from an oral swab of the test animal, biological material obtain from a body swab of the test animal, and tissue from the test animal.

In an embodiment of the method, the one or more pathogens is selected from the group consisting of: *Staphylococcus* spp., *Pasteurella* spp., *Proteus* spp., *Klebsiella* spp., *Giardia* spp., *Cryptosporidium* spp., *Entamoeba* spp., *Spironucleus* spp., Murine norovirus, *Pseudomonas* spp., and beta-hemolytic *Streptococcus* spp.

In an embodiment of the method, isolating the plurality of nucleic acids includes at least one of magnetic isolation, column-based nucleic acid isolation, organic extraction methods, and alkaline lysis.

In an embodiment of the method, the collection media includes a filter selected from the group consisting of mechanical filters, chemical filters, electrostatic filters, and wet scrubbers.

In an embodiment of the method, the collection media possesses an efficiency selected within the range between 5% to 40%.

In an embodiment of the method, the collection media is a graded filter.

In a further embodiment, a system for collecting environmental air dust is provided. The system includes a reversibly sealable enclosure. The enclosure includes a chamber adapted to receive a cage for housing an animal, the cage being in fluid communication with the chamber, an air intake coupleable with an air supply, and an air return coupleable with a vacuum source, where a portion of a flow of supplied air directed through the chamber, from the air supply to the air exhaust, passes through at least a portion of the cage when received in the chamber and is sufficient to transport a portion of environmental air dust contained within the received cage to the air exhaust. The system further includes an actuation device in mechanical communication with the enclosure, the actuation device operable to agitate the contents of the cage when received within the chamber, and a collection media suitable for capturing at least a portion of the environmental air dust transported by a flow of air directed through the chamber.

Embodiments of the system may include one or more of the following, in any combination.

In an embodiment of the system, the collection media is positioned with respect to the enclosure such that the collection media impinges at least a portion of the flow of air after passage through the cage.

In an embodiment of the system, the collection media is positioned within the enclosure and outside of the cage.

In an embodiment of the system, the collection media is positioned with respect to the enclosure such that the collection device impinges at least a portion of the flow of air after passage through the air return.

In an embodiment of the system, at least a portion of the collection media is positioned on a wall of the cage.

In an embodiment of the system, at least a portion of the collection media is suspended within the cage.

In an embodiment of the system, the collection media includes a filter selected from the group consisting of mechanical filters, chemical filters, electrostatic filters, and wet scrubbers.

In an embodiment of the system, the actuation device is operable to reversibly move the enclosure at least one of translationally and rotationally with respect to an initial position.

In an embodiment of the system, the actuation device is an ultrasonic device.

BRIEF DESCRIPTION OF THE DRAWINGS

The foregoing and other objects, features and advantages will be apparent from the following more particular description of the embodiments, as illustrated in the accompanying drawings in which like reference characters refer to the same parts throughout the different views. The drawings are not necessarily to scale, emphasis instead being placed upon illustrating the principles of the embodiments.

DETAILED DESCRIPTION

Figure 1:
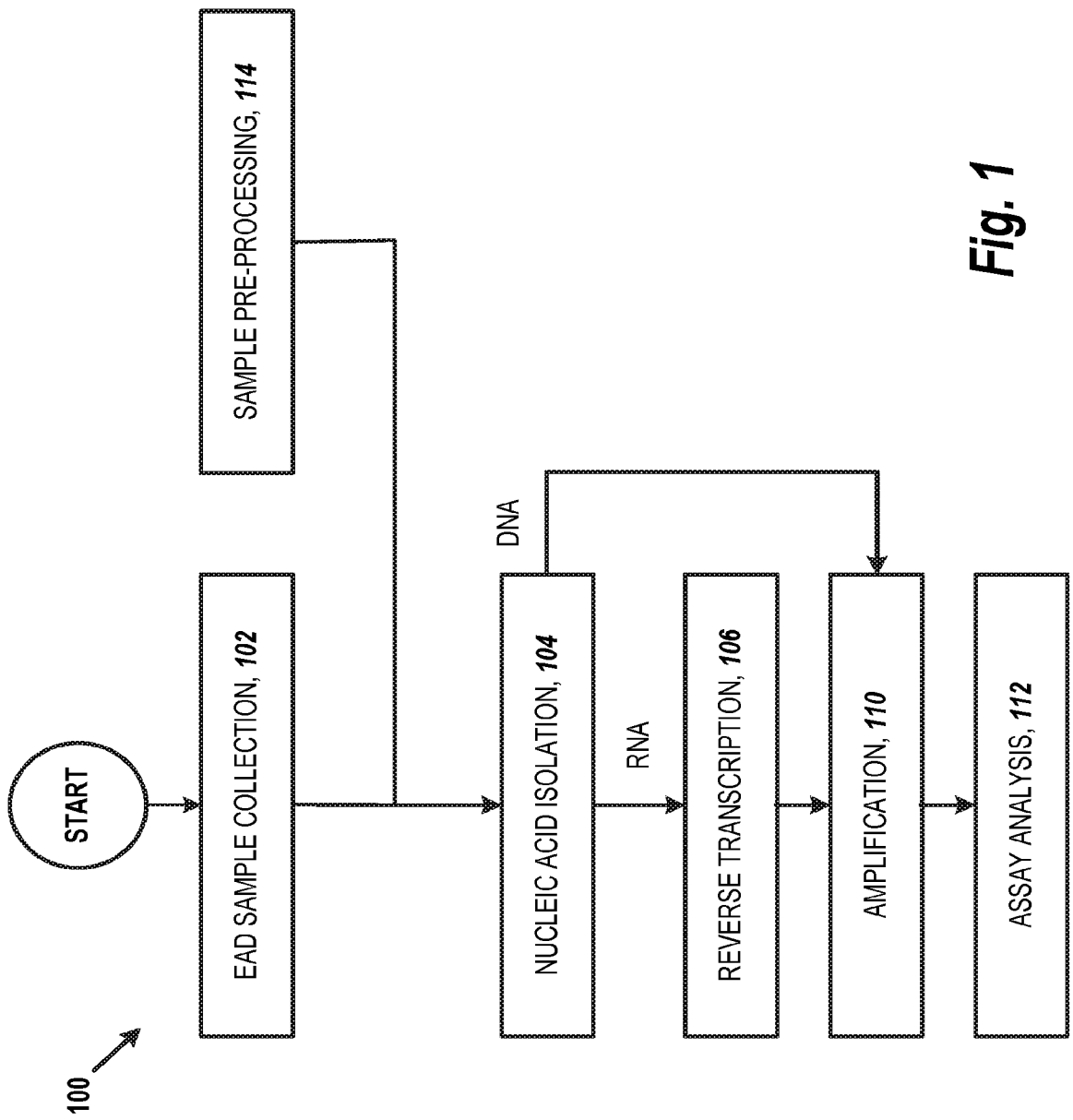
FIG. 1 is a schematic flow diagram illustrating an embodiment of a method for collecting and analyzing Environmental Air Dust (EAD) from an individually ventilated cage rack (IVR) for identification of pathogens contained therein.

Embodiments of the present disclosure are directed to systems and methods for collection and analysis of environmental air dust (EAD). In certain embodiments, the systems and methods may be employed in combination with micro-isolator caging, such as static micro-isolator cages and individually ventilated cages (IVC) mounted in a rack. In alternative embodiments, the systems and methods may be employed in combination with non-IVC racks (e.g., open top or open cage racks where there is no air flow to accommodate collection of EAD).

Pathogen molecules, whether whole or fragments of a whole, are capable of attachment to air dust. This air dust, in turn, may be suspended in a flow of air and moved from one location to another. Thus, EAD collected from airflow passing through a pathogen rich environment may be analyzed to detect the presence of such pathogens within the cage environment.

In an embodiment, a method of detecting pathogens carried by environmental air dust includes collection of a test sample including EAD, isolation of a plurality of nucleic acids (e.g., RNA and/or DNA) representative of one or more infectious agents from the test sample, optional reverse transcription of RNA to cDNA if the isolated nucleic acids contain RNA, amplification of the cDNA and/or DNA (e.g., by polymerase chain reaction (PCR)), and assay interpretation. Optionally, as discussed below, the test sample may include biological material other than that captured by the collected EAD sample (e.g., fecal pellets, body swabs, oral swabs, tissue, etc.) to improve detection of low-copy organisms. In such circumstances, pre-processing of the non-EAD sample may be performed prior to nucleic acid co-isolation with the EAD sample.

The EAD sample is collected from a target environment such as an individually ventilated cage rack (IVR). In an IVR, a flow of sterile air is supplied to a first end of the rack and directed through cages of the rack (e.g., horizontally) to an opposing second end of the rack. EAD, and pathogens attached thereto, are carried by the airflow from their respective cages out of the rack. A plurality of EAD collection media, suitable for capturing at least a portion of the EAD, are positioned in the airflow path. Thus, during use of the ventilated rack, the plurality of EAD collection media impinge at least a portion of the airflow, collecting EAD and attached pathogens from the cages.

In one embodiment, an EAD collection media is positioned within an exhaust channel that routes exhaust airflow away from the cages. In another embodiment, an EAD collection media is positioned on, adjacent, and/or within one or more cages.

In a further embodiment, a method of detecting pathogens carried by environmental air dust does not include collection of EAD within an individually ventilated cage rack (IVR) system. Instead, the EAD is collected from soiled bedding outside of an IVR (e.g., bedding soiled by a test animal). For example, in an embodiment, the method includes collecting EAD from a reversibly sealable enclosure housing an animal cage containing soiled bedding. The enclosure includes a chamber adapted to receive the animal cage, an air intake coupleable with an air supply, and an air return coupleable with a vacuum source. In use, a flow of air is provided through the enclosure, from the air intake to the air return. The soiled bedding is agitated to free dust containing pathogens into the air within the cage. In one embodiment, the bedding may be agitated by an animal placed within the cage (e.g., the test animal). In another embodiment, the enclosure is in communication with an actuation device which agitates the cage. The released EAD and attached pathogens are carried by the airflow out of the cage.

The plurality of EAD collection media are positioned so as to impinge at least a portion of the flow of air, allowing collection of EAD and attached pathogens. In one embodiment, an EAD collection media is mounted outside of the enclosure, within an exhaust channel that routes exhaust airflow away from the enclosure. In another embodiment, an EAD collection device is mounted on, adjacent to, and/or within the cage housed within the enclosure chamber.

EAD captured by the collection media may be subsequently analyzed to identify the presence of selected pathogens. This EAD analysis may be performed by techniques including, but not limited to, polymerase chain reaction (PCR) as noted above and discussed in greater detail below.

Notably, embodiments of the disclosed systems and methods may be employed to sample airborne pathogens attached to air dust from the environment of study animals directly, rather than requiring the use of sentinel animals. Beneficially, eliminating the use of sentinel animals avoids sentinel husbandry and the need for weekly bedding transfers, as well as saves rack space. Additionally, as shown in greater detail below, embodiments of the disclosed methods are capable of detecting infectious agents that do not transfer efficiently to bedding sentinels, as well as those which do transfer efficiently to bedding sentinels.

Embodiments of the disclosure will now be discussed with respect to the figures, beginning with FIGS. 1 and 2. FIG. 1 is a flow diagram of an embodiment of a method 100 for collecting and detecting pathogens carried by environmental air dust (EAD). As discussed in detail below, the method 100 includes receiving a test sample including environmental air dust in operation 102, isolating a plurality of nucleic acids (e.g., RNA and/or DNA) representative of one or more infectious agents from the EAD sample in operation 104, optional reverse transcription of RNA to cDNA if the isolated nucleic acids contain RNA in operation 106, amplification of cDNA and/or DNA in operation 110 (e.g., by polymerase chain reaction (PCR)), and assay interpretation in operation 112. In certain circumstances, the method 100 may optionally include sample pre-processing in operation 114.

Figure 2:
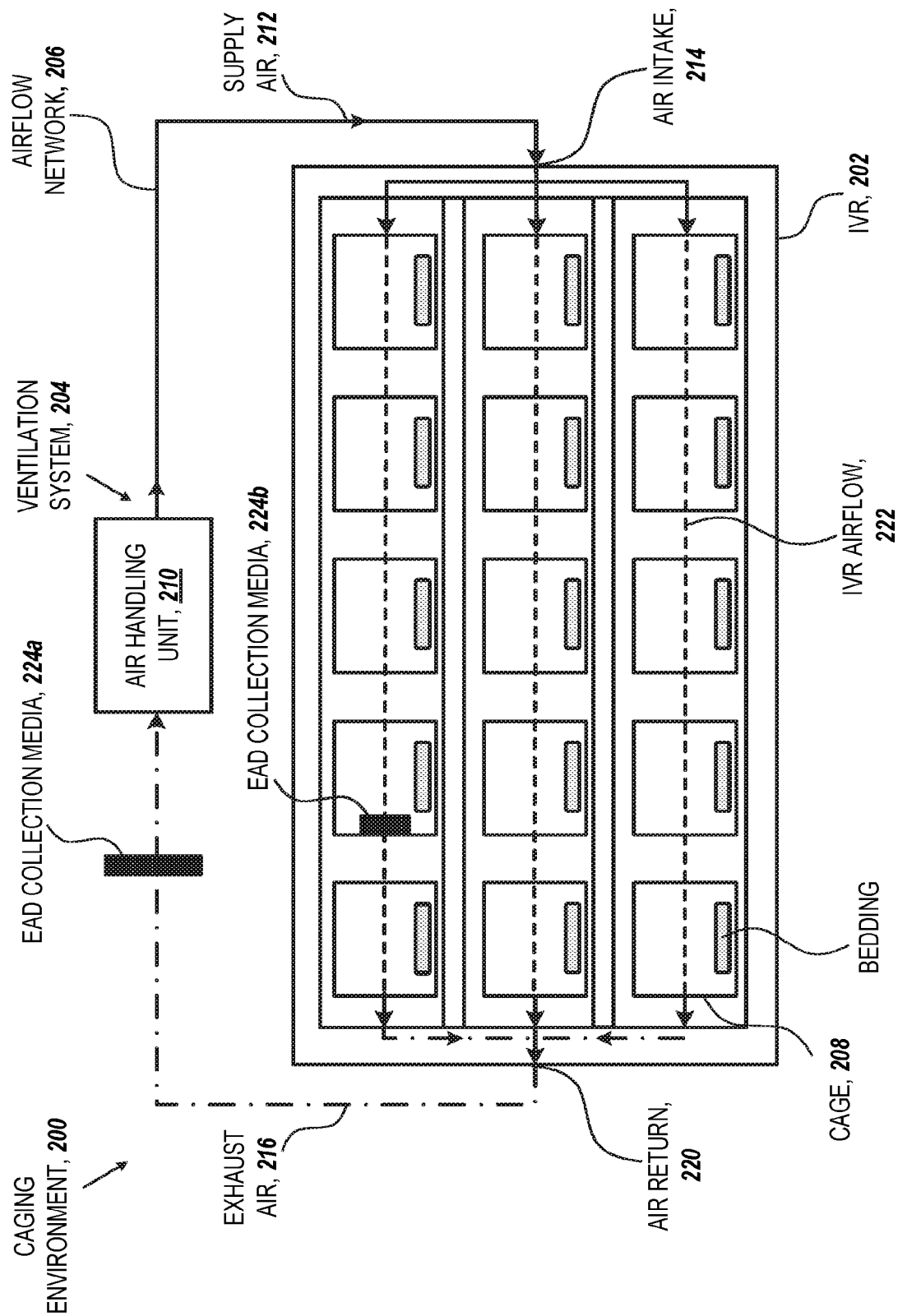
FIG. 2 is a schematic illustration of placement of a plurality of EAD collection media within an IVR environment.

FIG. 2 is a schematic illustration of an embodiment of a micro-isolator cage environment 200 from which the received EAD is collected. For the purpose of discussion, embodiments of the disclosure will be described in the context of an individually ventilated cage rack (IVR) 202 as the micro-isolator cage environment 200. However, it may be understood that the disclosed embodiments may be employed with any micro-isolator cages without limit.

The IVR 202 includes a plurality of cages 208 for housing animals (e.g., rodents) in a selected arrangement (e.g., an array having generally aligned rows and columns). The cage environment 200 further includes a ventilation system 204 in fluid communication with the IVR 202 via an airflow network 206. The ventilation system 204 includes an air handling unit 210 that provides sterile, conditioned supply air 212 to an air intake 214 of the IVR 202 and receives exhaust air 216 (e.g., air including dust and attached pathogen molecules) from an air return 220 of the IVR 202. In the IVR 202, the supply air 212 is distributed to different locations (e.g., different rows and/or columns) and flows through each cage 208. This airflow within the IVR 202, referred to as IVR airflow 222, is sufficient to transport at least a portion of EAD from respective cage locations through the air return 220. From the air return 220, airflow including the EAD travels to the air handling unit 210 and is referred to as exhaust air 216 herein.

The embodiment of FIG. 2 is illustrated with a closed ventilation system, where the exhaust air 216 is reconditioned (e.g., to a selected temperature, pressure, sterility, etc.) by the air handling unit 210 and subsequently provided to the IVR 202 as the supply air 212. However, in alternative embodiments, not shown, the ventilation system may be an open system, where the air supply is not provided from reconditioned air exhaust but is instead provided from a separate source.

A plurality of EAD collection media 224 (e.g. 224a, 224b) are further provided for capturing a portion of EAD within the IVR 202, while allowing the supply air 212, IVR airflow 222, and exhaust air 216 to move through the IVR 202 substantially unimpeded. Captured EAD may be retained on the surface of the EAD collection media 224, the bulk of the EAD collection media 224, and/or within a dedicated containment chamber, based on the configuration of the EAD collection media 224. Example EAD collection media 224 may include, but are not limited to, mechanical filters, chemical filters, wet scrubbers, electrostatic filters, and other filtering devices suitable for removing dust from air, without limit.

Each EAD collection media 224 may be independently selected to capture EAD having a size (e.g., diameter, cross-sectional area, or other selected dimension) approximately greater than a selected value. In other embodiments, the EAD collection media 224 may be graded (e.g., a graded filter), with spatial regions selected to capture EAD of different sizes. Such zones may vary continuously or discontinuously within the spatial extent of the EAD collection media 224. In certain embodiments, EAD collection media 224 may be selected to capture dust particles having a size ranging from about 0.1 nm to about 10 mm. In further embodiments, EAD collection media 224 may possess efficiency selected within the range between about 5% to about 40% for the selected size range. In certain embodiments, the efficiency of EAD collection media 224 may be approximately 30% for the selected size range. Further discussion of EAD collection media 224 may be found within U.S. Provisional application No. 62/280,057, filed on Jan. 18, 2016 and entitled "Method And System For Monitoring Air Flow Impurity," the entirety of which is incorporated by reference.

The position of the EAD collection media 224 may be varied, depending upon the configuration of the IVR 202. For example, as illustrated in FIG. 2, one or more EAD collection media 224a may be positioned within a portion of the airflow network 206 to capture EAD from the exhaust air 216. In alternative embodiments, one or more EAD collection media 224b may be positioned on or within one or more selected cages 208 to capture EAD from the IVR airflow 222. In further embodiments, at least one EAD collection media 224 may be positioned to capture EAD from both the exhaust air 216 and the IVR airflow 222.

Regardless of position, each the EAD collection media 224 is maintained in place for a selected time duration to capture EAD thereon. In certain embodiments, the selected time duration may be a minimum of 2 weeks. In further embodiments, the selected time duration may be 3-4 months. In further embodiments, the selected time duration may be one year or more.

Figure 4C:
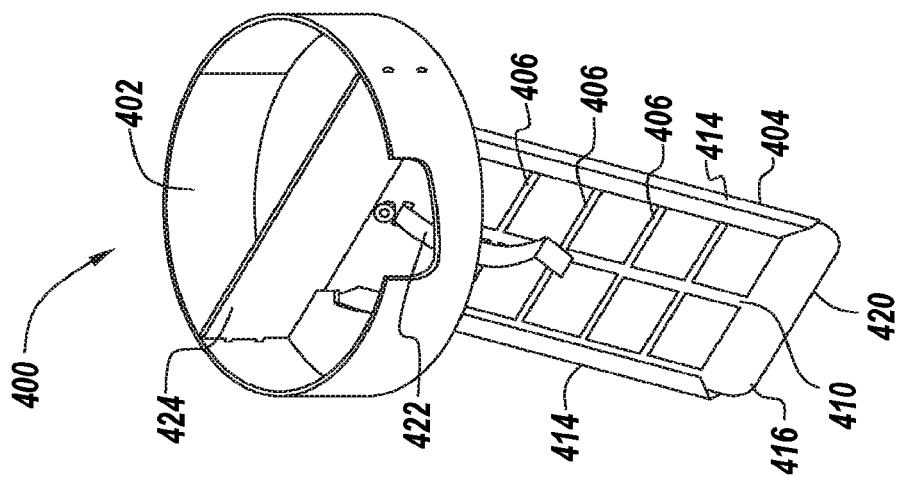
FIGS. 4A, 4B, and 4C illustrate embodiments of an EAD collection media holder for use within the IVR environment of FIG. 3A.
Figure 4B:
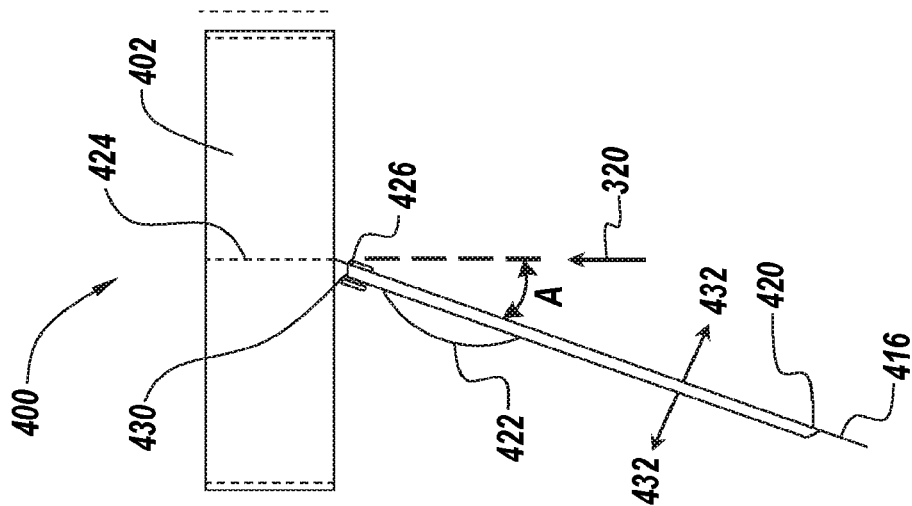
Figure 4A:
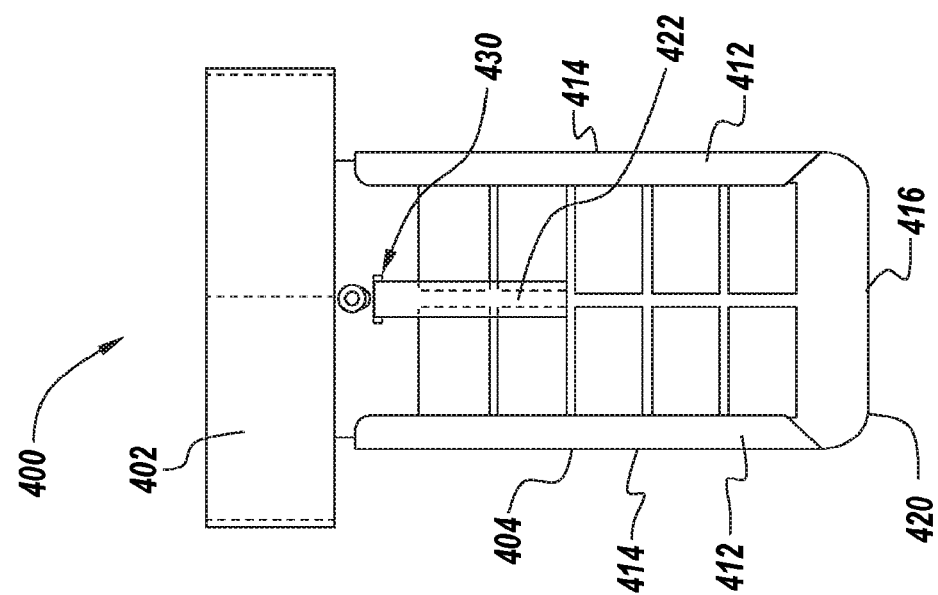
Figure 4D:
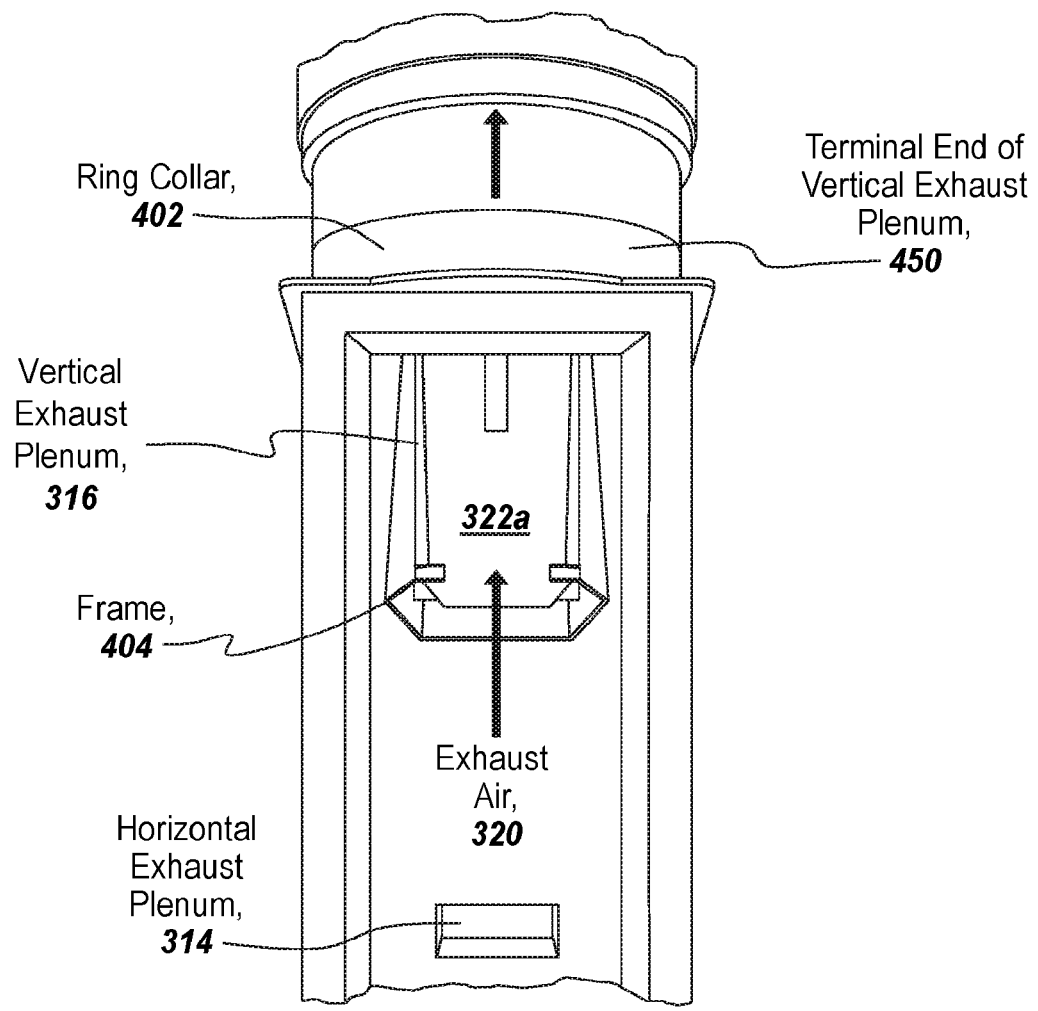
FIG. 4D is a photograph illustrating placement of an EAD collection media in a vertical exhaust plenum of the IVR.
Figure 4E:
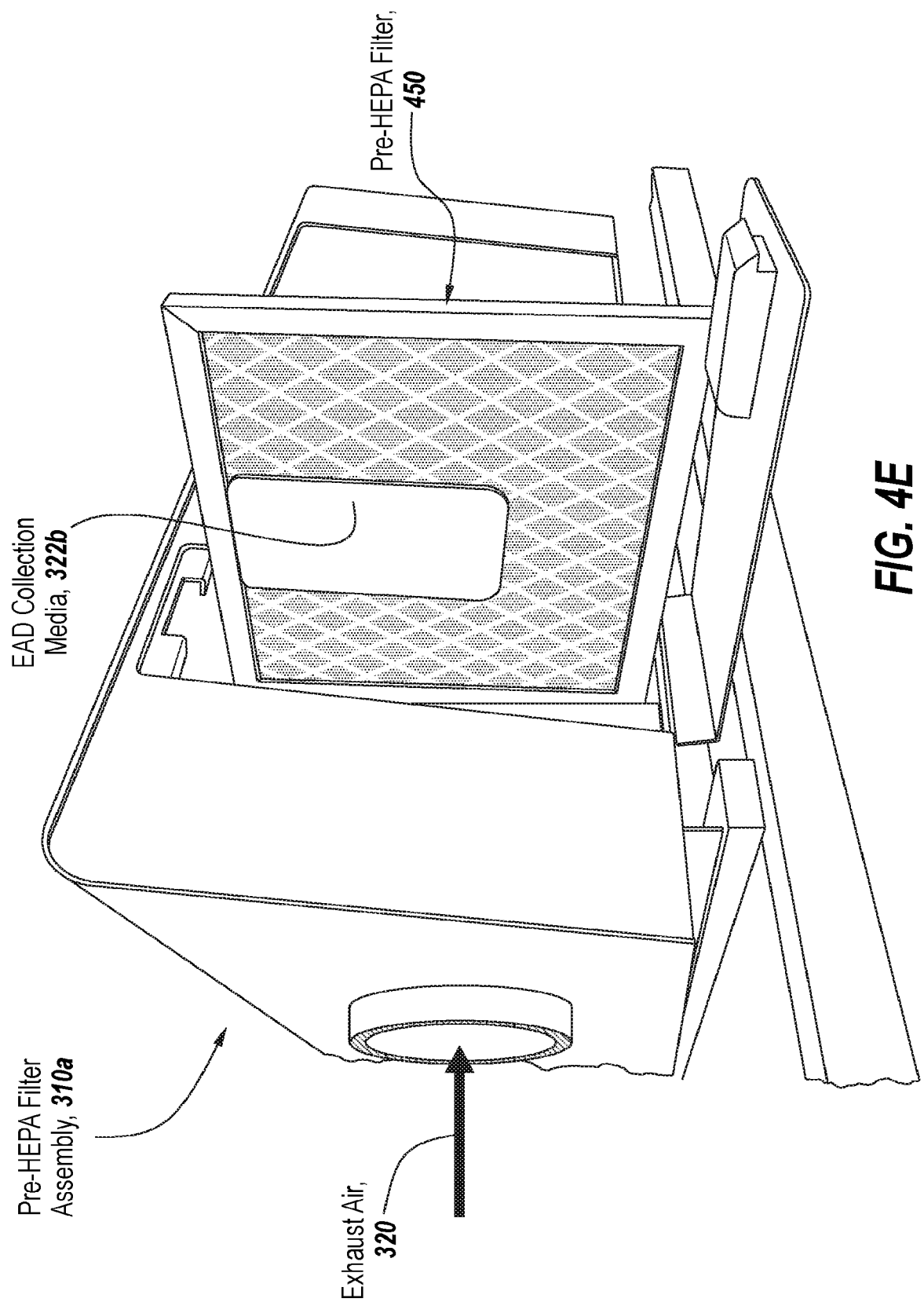
FIG. 4E is a photograph illustrating placement of an EAD collection media adjacent a pre-HEPA filter in fluid communication with the IVR.

In order to maintain sufficient ventilation within the IVR 202, the EAD collection media 224 may further deployed in a manner which does not substantially interfere with airflow within the ventilation system 204 (e.g., supply air 212, IVR airflow 222 and/or exhaust air 216). For example, as discussed in greater detail below with respect to FIGS. 3 and 4, the EAD collection media 224 may be understood to not substantially interfere with airflow when at least one of the following conditions are satisfied:

(i) a blower motor of the ventilation system 204 does not exhibit a change in RPM (speed) due to increased pressure caused by EAD collection media 322 (e.g. 322a, 322b, 322c) or the presence of an EAD collection media holder 400 (FIGS. 4A-4C) maintaining EAD collection media 322 (e.g., 322*a*) within a vertical exhaust plenum 316 (FIG. 4D);

(ii) a pressure within one or more cages 308 (FIG. 3A) varies by less than or equal to ±5% due to reduced airflow caused by a restriction in the vertical exhaust plenum 316 due to the presence of the EAD collection media 322*a* and/or the EAD collection media holder 400 as compared to the pressure within the one or more cages 308 absent the EAD collection media 322*a* and/or the EAD collection media holder 400 within the vertical exhaust plenum 316;

(iii) a pressure within the vertical exhaust plenum 316 (e.g., at an exhaust collar or terminal end 452 of the vertical exhaust plenum 316) varies by less than or equal to ±10% due to the presence of the EAD collection media 322*a* and/or the EAD collection media holder 400 within the vertical exhaust plenum 316 as compared to the pressure within the vertical exhaust plenum 316 absent the EAD collection media 322*a* and/or the EAD collection media holder 400.

In further embodiments, the configuration of the EAD collection media 224 and/or the positioning of the EAD collection media 224 within the IVR 202 facilitates maintenance of sufficient ventilation within the IVR 202. In one embodiment, respective dimensions of the EAD collection media 224 may be less than (e.g., 30% less, 40% less, 50% less, 60% less, 70% less, etc.) than corresponding dimensions of an airflow passageway in which the EAD collection media 224 is positioned or adjacent to (e.g., vertical exhaust plenum 316, pre-HEPA filter 450, etc.). In another embodiment, described in greater detail below, the EAD collection media 224 may be placed such that the plane of the EAD collection media 224 is oriented at an acute angle with respect to a direction of airflow (e.g., vertical airflow within the vertical exhaust plenum 316) during capture of the dust sample. The acute angle may be selected within the range from 15° to 25° (e.g., 20°) with respect to the direction of airflow within the vertical exhaust plenum 316.

Following collection of EAD by capture using the EAD collection media 224, at least a portion of the collected EAD is analyzed to detect the presence or absence of a pathogen in operations 104-112. To minimize handling and contamination of the EAD, and facilitate transport, the EAD collection media may be removed from the IVR environment 200 and directly placed in a sterile container (e.g., a reversibly sealable tube).

In certain embodiments of the method, receiving a test sample including captured EAD may include receiving the captured EAD itself. In other embodiments, receiving a test sample including captured EAD may include receiving the captured EAD while still retained on the EAD collection media. In further embodiments, receiving a test sample including captured EAD may include collecting the EAD from airflow, as discussed herein.

With continued reference to FIG. 1, certain embodiments of the method 100 may include a pre-processing operation 114 for preparation of a non-EAD sample to be analyzed with collected EAD samples. Examples of such non-EAD samples may include, but are not limited to, one or more of fecal pellets, biological material collected from oral swabs, biological material collected from body swabs, and tissue.

For example, assume that the non-EAD sample is fecal pellets. The pre-processing operation 114 processes the fecal pellets into a slurry for later use in isolating nucleic acids for testing. Fecal pellets may be collected from rack cages. In further embodiments, fecal pellets may be obtained from different rodent lines and adult rodents in target optimal age ranges (e.g., 6-10 weeks). Once obtained, one or more of the fecal pellets are transferred to a micro-centrifuge tube with one or more stainless steel ball bearings. A selected amount of phosphate buffered saline (PBS) is added to the tube containing the fecal pellet(s) to form a fecal pellet sample. The fecal pellet sample is disrupted in a mixer mill for a selected time at a selected frequency and subsequently centrifuged. Subsequently, the fecal sample may be pooled with collected EAD for nucleic acid co-extraction.

Because fecal pellets contain bile acids, hemoglobin breakdown products, complex polysaccharides, and other compounds that may inhibit amplification, the pre-processing operation 114 is performed to concentrate agents of interest (e.g., viruses, bacteria, and other micro/macrobiological material associated pathogens) for nucleic acid isolation, yet also excluding as much as the fecal content as possible.

Because the pre-processing operation 114 concentrates agents of interest, performing pre-processing operation 114 as part of the method 100 may be beneficial to improve detection of low copy organisms. Examples of low copy organisms may include, but are not limited to, *Staphylococcus* spp. (bacteria), *Pasteurella* spp., *Proteus* spp., *Klebsiella* spp. (bacteria), *Giardia* spp. (protozoa), *Cryptosporidium* spp. (protozoa), *Entamoeba* spp. (protozoan), *Spironucleus* spp. (protozoan), Murine norovirus (virus), *Pseudomonas* spp., and beta-hemolytic *Streptococcus* spp.

In operation 104, the test sample including collected EAD, optionally pooled with non-EAD material pre-processed in operation 114, is further processed to isolate nucleic acids therefrom (e.g., RNA, DNA, and combinations thereof). In certain embodiments, the nucleic acid isolation is performed by magnetic isolation. Magnetic isolation, although limited in the total yield, does provide a highly purified nucleic acid. In the inventor's experience, magnetic isolation includes better recovery of RNA versus other column methods as well as an observed reduction of PCR inhibitors. However, it may be understood that alternative processes for nucleic acid isolation may be employed, alone or in combination with magnetic isolation, without limit. Examples of such alternative isolation processes include, one or more of column-based nucleic acid isolation, organic extraction methods, and alkaline lysis.

In further embodiments, a nucleic acid recover control (NARC) may be optionally added to the isolated nucleic acids in operation 104. The NARC is a unique algae RNA (or DNA when only DNA tests are performed). By adding the NARC to the lysis buffer, it allows monitoring of any sample type and provides verification that any nucleic acid present at the lysis step was successfully recovered. Some samples may contain little or no nucleic acid and others may have great variation, so measuring optical density to determine nucleic acid content is not useful. Accordingly, successful extraction (recovery of nucleic acid) as well as a successful reverse transcription reaction are each verified by performing a separate assay for the NARC template as part of the controls run during the amplification test analysis.

In operation 106, when RNA is present, alone or in combination with DNA, the RNA is reverse transcribed into cDNA, which is required for RNA viruses. Alternatively, if only DNA is present in the isolated nucleic acid, this reverse transcription operation may be omitted.

Following reverse transcription, amplification is performed in operation 110. In an embodiment, amplification may be performed by loop mediated isothermic amplification or polymerase chain reaction (PCR). Examples of PCR include, but are not limited to, endpoint PCR (e.g., agarose electrophoresis, hybridization arrays, etc.) and real-time PCR (e.g., molecular beacon PCR, TaqMan PCR, SYBR Green PCR, etc.).

In an embodiment, the amplification is performed by TaqMan PCR. Samples that are evaluated for small panels of agents are evaluated on a 96-well or 384-well real-time TaqMan PCR platform. Samples that are evaluated for large panels of agents are first pre-amplified then amplified by real-time TaqMan PCR on an open array. A DNA spike control to monitor for PCR inhibition is also added at the pre-amplification step for panels evaluated on the open array. For 96 and 384-well formats, the spike is added as a separate assay during the PCR testing for all samples.

A PCR Assay is subsequently performed for detection of selected infectious agents. Approximately 100 copy templates are prepared by cloning target sequences into plasmid vectors and used as positive control templates. About 1000 copy plasmids are also included for open array testing. Negative template wells are used for all formats. NARC and spike control mock samples processed alongside of field samples are evaluated to demonstrate function of these control templates and assays.

In operation 112, an analysis of the assay is performed. Following PCR amplification, Ct values (threshold cycle) are measured for samples and the samples are evaluated based upon the measured Ct values. The Ct values are a relative measure of the concentration of target in the PCR reaction. Further information regarding specimen analysis may be found in "Efficacy of Direct Detection of Pathogens in Naturally Infected Mice by Using a High-Density PCR Array," *J. Am Assoc. Lab Anim. Sci.* Vol. 52, No. 6, pgs. 763-772 (2013), the entirety of which is incorporated herein by reference.

EXAMPLES

In the following examples, low prevalence infection was simulated on an IVR. Samples of EAD were collected by use of collection devices in-line with airflow. Comparative samples were collected from soiled bedding sentinels and swabs. All collected samples were separately analyzed using PCR according to embodiments of the method 100 of FIG. 1 discussed above. Samples obtained from soiled bedding sentinels were further analyzed by traditional screening (e.g., serology, bacterial culture, parasitology).

Methodology

Study Design

Infectious agent source: Pet shop mice were placed in 4 cages on each rack side. Two mice were housed in each cage, one 3-4 weeks old and the other 6-10 weeks old. Assuming 80 total cages on the rack, these conditions simulated a prevalence of about 5% on rack (4/80 cages).

Sentinel animals: 4 cages of CD-1 Elite bedding sentinels were provided on the IVR. 3 sentinel mice were provided per cage. 1 mouse per cage per month was submitted for PCR and traditional testing (total of 4 per month).

Simulation of a low prevalence: 5% "true dilution" soiled bedding from the pet shop mice was placed with the sentinel mice. The soiled bedding was diluted with soiled bedding from gnotobiotic mice to achieve the desired concentration.

All cages were placed in furthest locations from incipient EAD swab sites.

Exhaust Air Dust Sample Collection

Figure 3A:
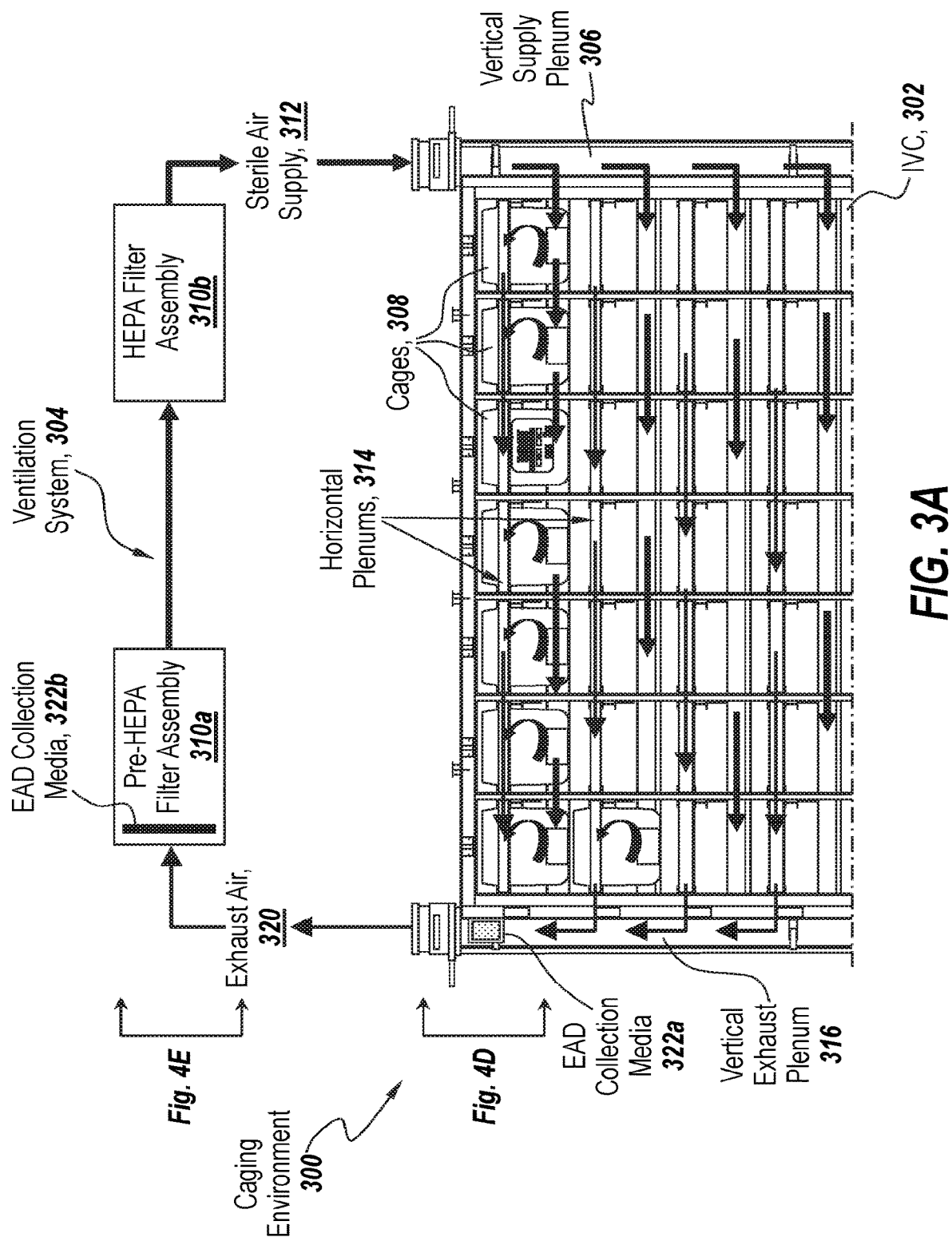
FIG. 3A is a schematic illustration of placement of a plurality of EAD collection media within an IVR environment.

With reference to FIGS. 3A-3B and 4A-4C, collection of EAD samples by in-line EAD collection media and swab will now be discussed. FIG. 3A presents a schematic illustration of an embodiment of a cage environment 300 including an IVR 302 housing cages 308 in fluid communication with a closed ventilation system 304 from which EAD is collected in the instant examples. A supply of sterile air 312 is delivered to a generally vertical supply plenum 306 of the IVR 302 from the ventilation system 304. The vertical supply plenum 306 directs the sterile supply air 312 through the cages 308 via a plurality of generally elongated horizontal plenums 314 from the vertical supply plenum 306 to an opposing second end of the rack including a generally vertical exhaust plenum 316. EAD and pathogens attached thereto are carried by IVR air flow 320 through respective cages 308 out of the IVR 302 as exhaust air 320. The ventilation system 304 includes a pre-HEPA filter assembly 310a and a HEPA filter assembly 310b. The pre-HEPA filter assembly 310a receives the exhaust air 320. Air flowing through the pre-HEPA filter assembly 310a is directed into the HEPA filter assembly 310b, where it exits as supply air 312.

A plurality of EAD collection media 322a, 322b are further positioned to capture EAD while not interfering with airflow through the IVR 302. A first EAD collection media 322a is a physical filter suspended near a top of the vertical exhaust plenum 316, referred to herein as exhaust plenum filter 322a.

With further reference to FIGS. 4A-4D, the exhaust plenum filter 322a is supported within the vertical exhaust plenum 316 by an EAD collection media holder 400. The holder 400 includes a ring collar 402 attached to a frame 404. As discussed in greater detail below, in use, the ring collar 402 can be slip fit into a terminus 452 of the vertical exhaust plenum 316.

In an embodiment, the holder 400 and frame 404 can be formed of metal or plastic. In one embodiment, the frame 404 is formed of stainless steel and the ring collar 402 is welded to the frame 404. The frame 404 can be formed of a plurality of horizontal members 406 extending from vertical member 410 to form a grid pattern. Vertical lip 412 can be positioned at outer edges 414 of the frame 404. The grid pattern retains the EAD collection media 224 and provides sufficient contact of exhaust air 320 with the exhaust plenum filter 322a.

The frame 404 can be rotated in the directions of arrows 432 for positioning the frame 404 an angle, A, with respect to exhaust air 320 within the vertical exhaust plenum 316. This positioning tailors the degree of contact of exhaust air 320 with the exhaust plenum filter 322a (e.g., flow of exhaust air 320 along the length of the exhaust plenum filter 322a). This adjustability is beneficial for minimizing the impact of the exhaust plenum filter 322a on airflow within the IVR 202. A horizontal lip 416 at an end 420 of the frame 404 can further generate turbulence within the exhaust air 320 flowing over collection media holder 400 to facilitate EAD capture from the exhaust air 320.

A spring clip 422 can be attached to center mount 424 of ring mounting 112 by inserting an end 426 of the spring clip 422 through a slot 430 in the center mount 424. The spring clip 422 secures the EAD collection media 322a to the frame 404. Moving the spring clip 422 away from the plane of the frame 404 allows insertion or removal of the exhaust plenum filter 322a from the EAD collection media holder 400.

Figure 5C:
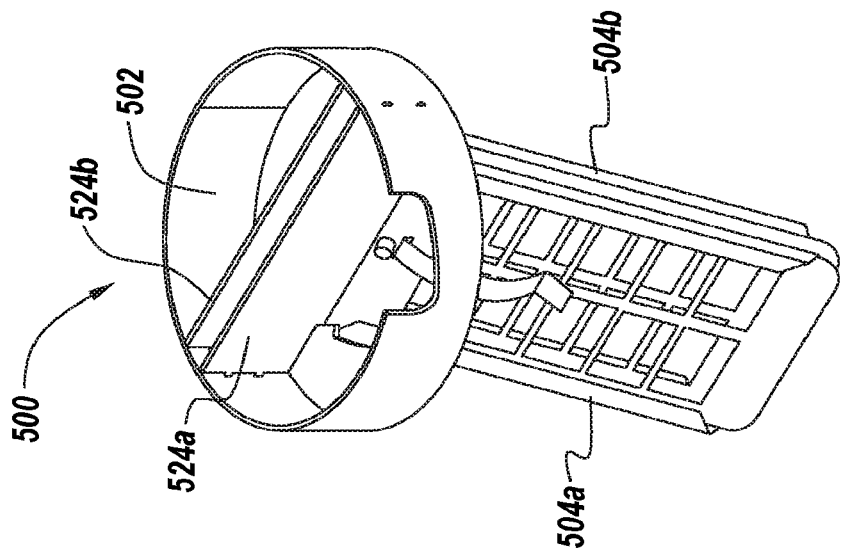
FIGS. 5A, 5B, and 5C illustrate a second embodiment of an EAD collection media holder for use within the IVR environment of FIG. 3A.
Figure 5B:
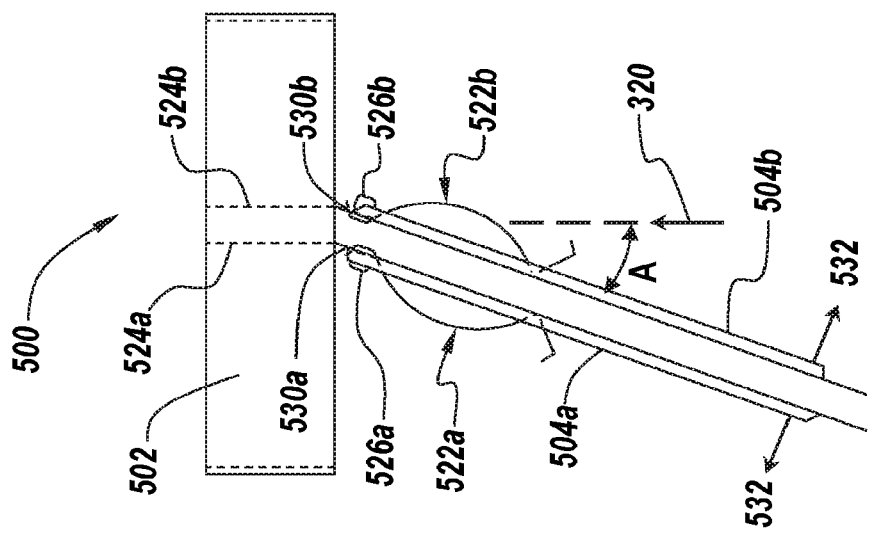
Figure 5A:
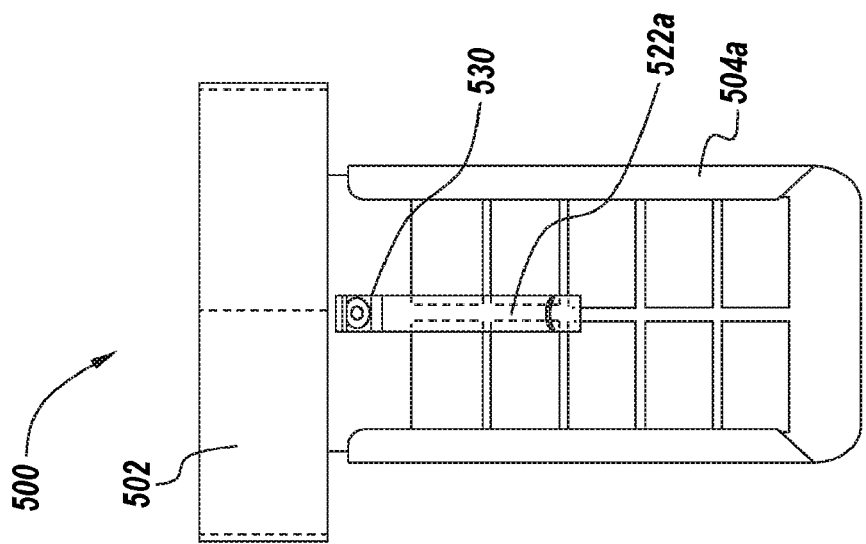

FIGS. 5A-5C show an alternate embodiment of a EAD collection media holder 500 for support of exhaust plenum filter 322a. Ring collar 502 can be attached to a plurality of frames, such as 504a, 504b. The ring collar 502 and frames 504a, 504b are as discussed previously with respect to ring collar 402 and frame 404 except as outlined below. Ring collar 502 can be slip fit into the terminus 452 of the vertical exhaust plenum 316. Each of the EAD collection media holder frames 504a, 504b can be angled in the direction of arrows 532 at an angle A with respect to exhaust air 320 within the vertical exhaust plenum 316. This positioning allows the degree of contact of exhaust air 320 with the exhaust plenum filter 322a (e.g., flow of exhaust air 320 along the length of the exhaust plenum filter 322a) to be adjusted. This adjustability is beneficial for minimizing the impact of the exhaust plenum filter 322a on airflow within the IVR 202.

Spring clip 522a can attach the EAD collection media holder 500 to center mount 524a of ring mounting 502 by inserting end 526a of spring clip 522a through slot 530a in center mount 524a. Spring clip 522b can attach the EAD collection media holder 504b to center mount 524b of ring collar 502 by inserting end 526b of the spring clip 522b through the slot 530b in center mount 524b. The spring clips 522a, 522b provide clamping of EAD collection media 224a as shown in FIG. 5B. Moving the spring clip 522a, 522b away from the plane of their respective frame 504a, 504b allows insertion or removal of the EAD collection media 224a from the EAD collection media holder 500.

Figure 6A:
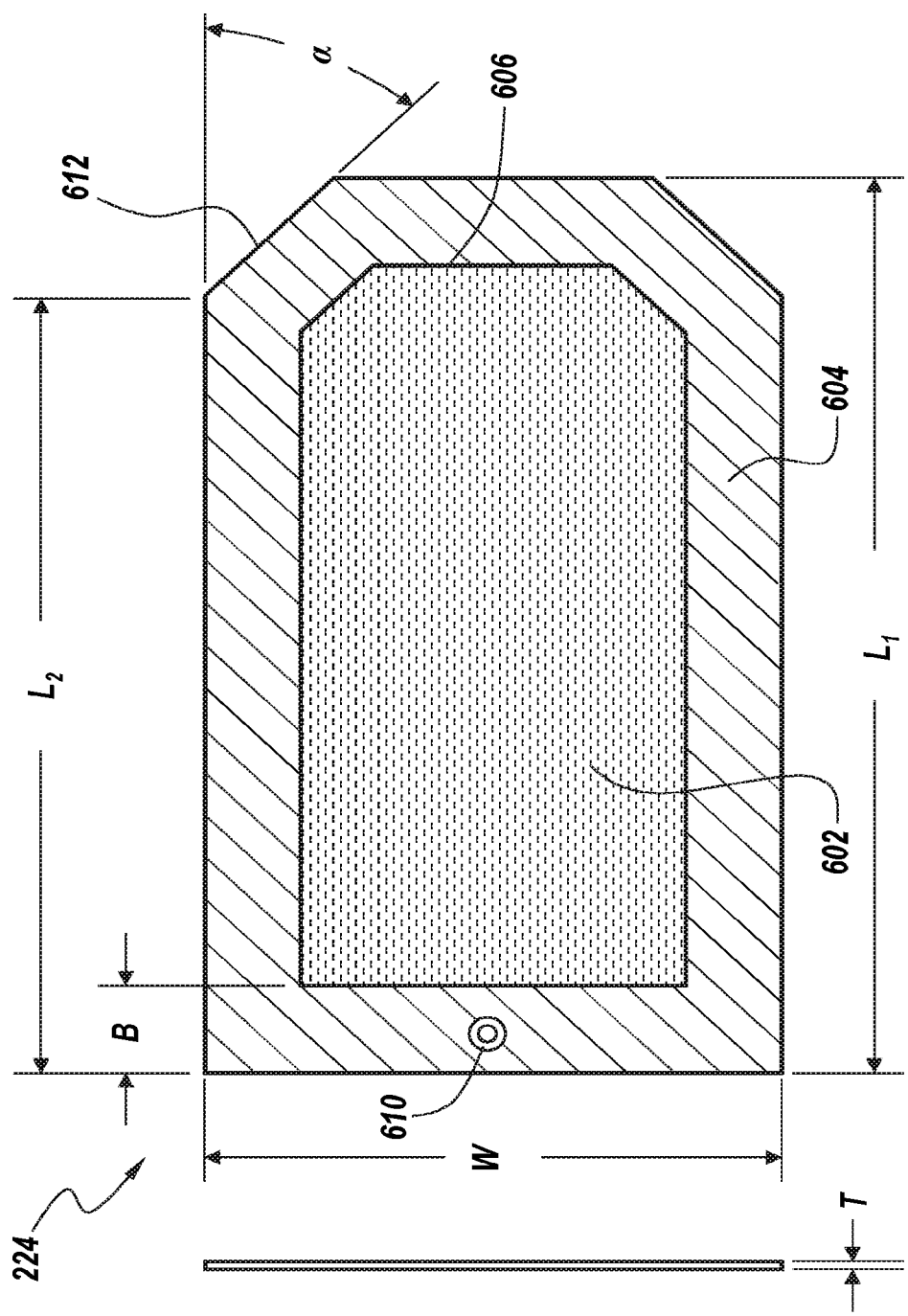
FIGS. 6A and 6B are schematic illustrations of embodiments of EAD collection media.
Figure 6B:
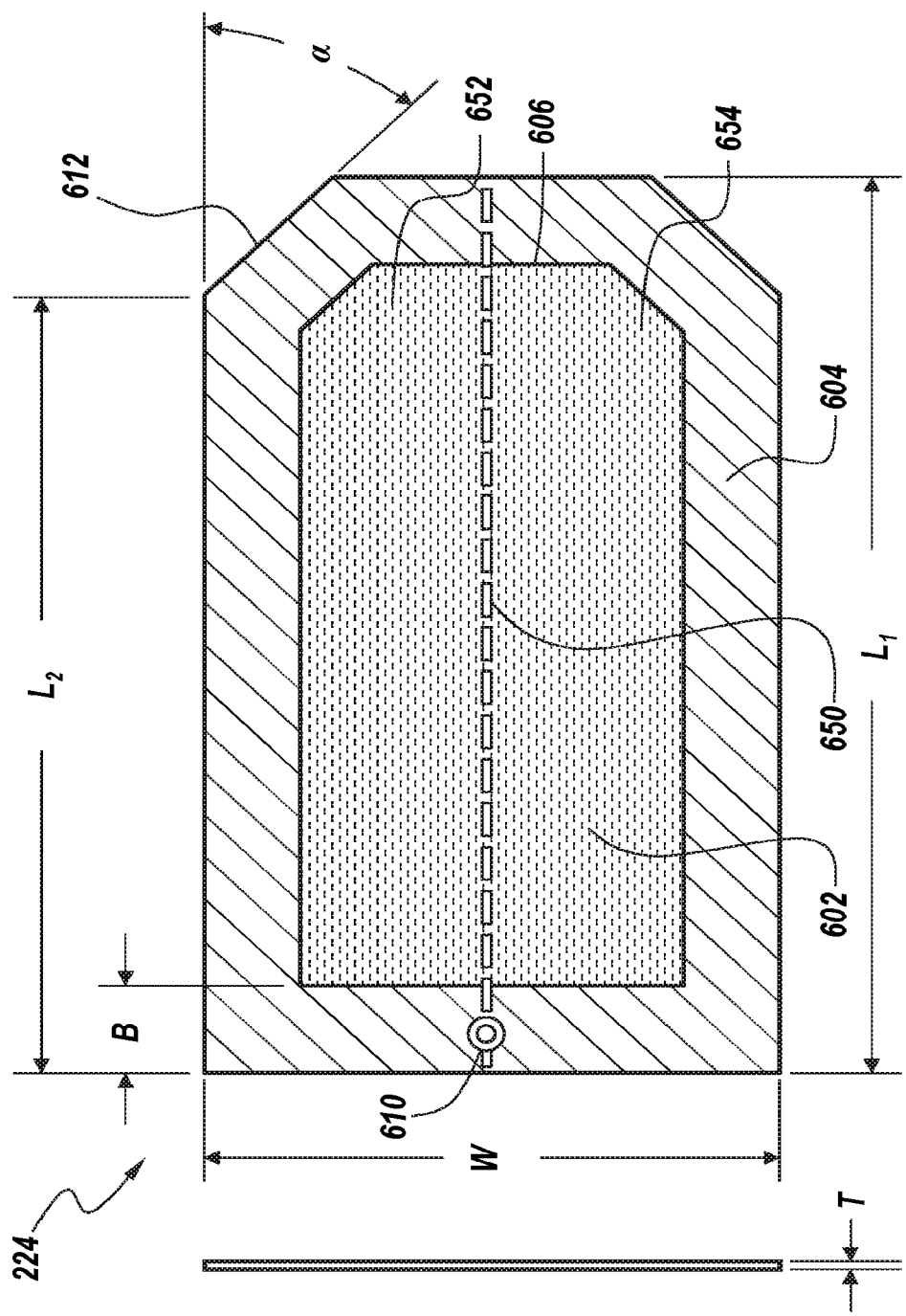

FIGS. 6A-6B are schematic illustrations of embodiments of EAD collection media 224 suitable for use one or more of EAD collection media (e.g., 224a, 224b, 322a, 322b, 322c). EAD collection media 224 includes media 602 coupled to a media frame 604. The media frame 604 extends around an outer edge 606 of the media 602. In one embodiment, the media 602 is heat sealed to the media frame 604 for provide a more rigid structure that facilitates handling, insertion, and removal of the media 602 (e.g., from EAD media holder 400, 500). The media frame 604 may optionally be marked with indicia 610 (e.g., a dot or notch) for use in identifying a direction of insertion of the EAD collection media 224 into EAD collection media holder 400, 500. The media frame 604 may further include one or more chamfers 612 at positioned at an angle $\alpha$ with respect to its longitudinal edges.

In an embodiment, the media 602 can be constructed of an electrostatic and controlled gradient structure including thermally woven polypropylene/polyethylene fibers, spun bond, continuous filament and attracts both positively and negatively charged particles with low moisture regain. The media 602 can prevent fibers from swelling due to moisture absorbed from the air stream. In one embodiment, the media 602 is white. The media 602 can carry a varying MERV (Minimum Efficiency Rating Value) rating between about 6 and about 10 (e.g., 8). In further embodiments, the media 602 may possess a basis weight of 2.00 oz/yd$^2$, thickness 64 mils, and Frazier Air Permeability 490 cfm/ft$^2$. In other embodiments, the polypropylene fibers of media 602 can be substituted by polyolefin fibers.

In an embodiment, the frame 604 can be manufactured of various synthetic fibers (e.g., polyester fibers). In one embodiment, the frame 604 also functions as a collection media. For example, the frame 604 may include a white spun collection media with a basis weight of 8.0 oz/yd$^2$, nominal thickness of 23 mils. strip tensile MD of 125 ft. lb/0.6 in. In further embodiments, the frame 604 can be constructed of any of collection media that can be heat sealed to EAD media 602 and has a basis weight between 6 and 10.

FIG. 6B shows an alternative embodiment of the EAD collection media 224 including a perforation 650. Perforation 650 is positioned between a first side 652 and a second side 654 of EAD collection media 224. The perforation 650 can be separated to separate the first and second sides 652, 654 of EAD collection media 224 from one another.

In a non-limiting embodiment, the dimensions of the EAD collection media 224 are as follows. A total length, $L_1$, of the EAD collection 224 is 3.75 in. A length, $L_2$, from a first end of the media frame 604 to chamfer 612 is 3.25 in. A frame border, B, is 0.375 in. An EAD Collection media width, W, is 2.312 in. An EAD collection media thickness, T, is less than or equal to 0.032 in. It may be understood that the above dimensions are provided for the purpose of example and that the EAD collection media 224 may possess other dimensions, as necessary.

During EAD collection, the ring collar 402 or 502 is mounted adjacent a top end of the vertical exhaust plenum 316 (FIG. 4D). So positioned, the exhaust plenum filter 322a is suspended within the vertical exhaust plenum 316 with angle A set as an acute angle between plane of the exhaust plenum filter 322a and a flow direction of the exhaust air 320. In an embodiment, the acute angle is selected within the range of 15° to 25° (e.g., 20°) with respect to the direction of airflow within the vertical exhaust plenum 316. In further embodiments, the in-plane dimensions of the exhaust plenum filter 322a may be also smaller than the cross-sectional dimensions of the vertical exhaust plenum 316. In this manner, EAD may be captured from the exhaust air 320 without substantially interfering with the flow of exhaust air 320.

As further illustrated in FIGS. 3A and 4C, EAD was also collected using a second EAD collection media 322b (a physical filter) attached to a leading face (upstream facing) of a pre-HEPA filter 450 of the pre-HEPA filter assembly 310a. Each of the EAD collection media 322a, 322b were deployed for 3 months. As each of the EAD collection media 322a, 322b capture EAD from the exhaust air 320 (i.e., air that has passed through the extent of the IVR 302), any EAD collected is expected to be representative of the IVR 302 as a whole.

Figure 3B:
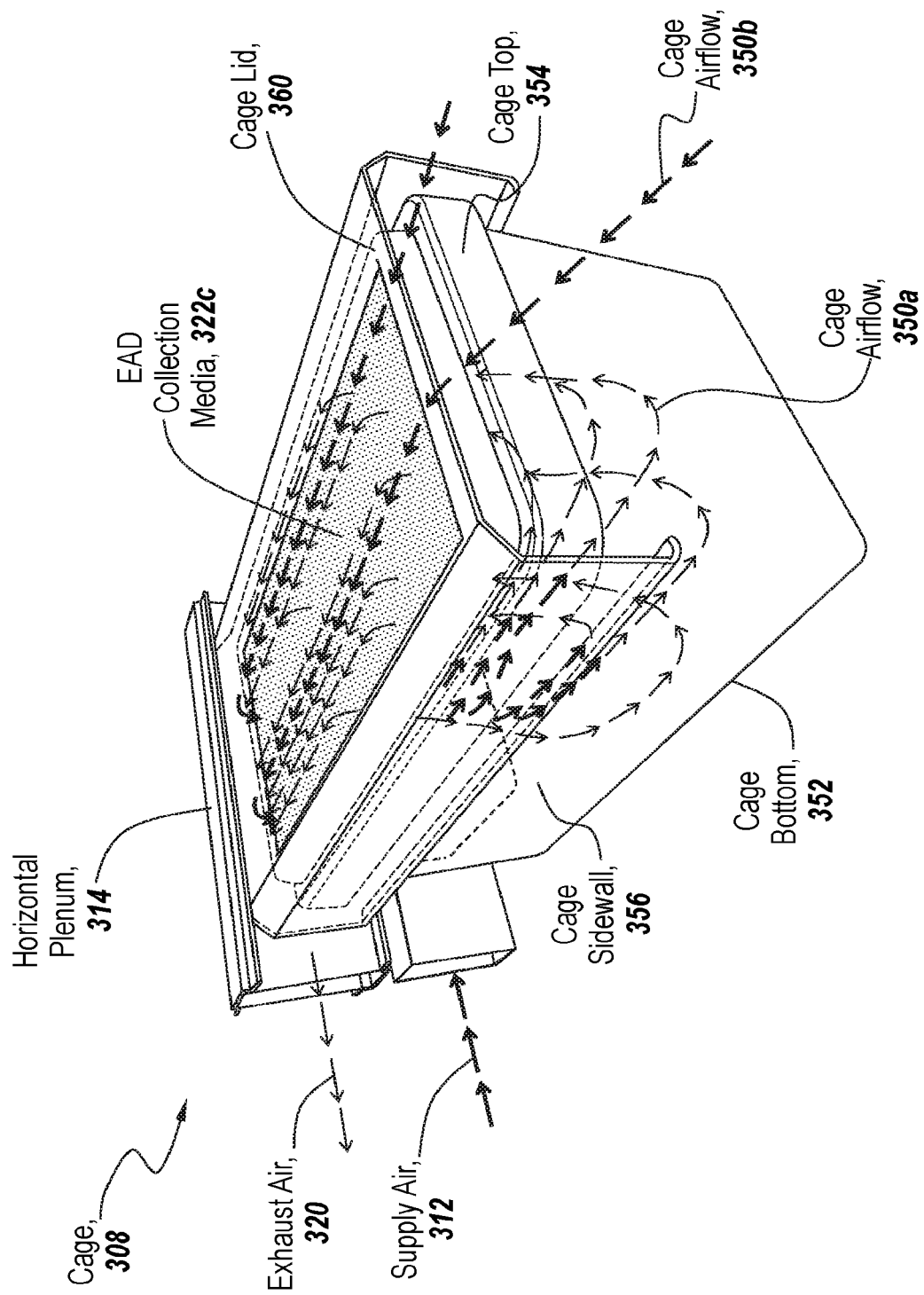
FIG. 3B is a schematic illustration of an embodiment of a cage including an EAD collection media positioned on-cage for use in collecting EAD from the cage within an IVR environment.

As additionally illustrated in FIG. 3B, EAD was further collected from airflow 350a, 350b within and/or adjacent cages 308 containing soiled bedding (not shown). Each cage 308 included a bottom 352, a top 354, sidewalls 356, a porous cage lid 360, and a third EAD collection media 322c. The third EAD collection media 322c (a physical filter) was placed on the cage top 354, which is in fluid communication through the porous cage lid 360 with airflow 350a circulating through an interior volume of the cage 308 as well as airflow 350b passing over the porous cage lid 360. However, it may be understood that, in alternative embodiments, EAD collection media may be positioned on any cage sidewall, within any cage, or adjacent to any cage, as appropriate. A new EAD collection media 322c (2" or 2.5"×3") was placed on each cage top 354 at the beginning of the study and every 3 months thereafter. The cage top 354 was further transferred each time the cage 308 was cleaned.

Figure 7B:
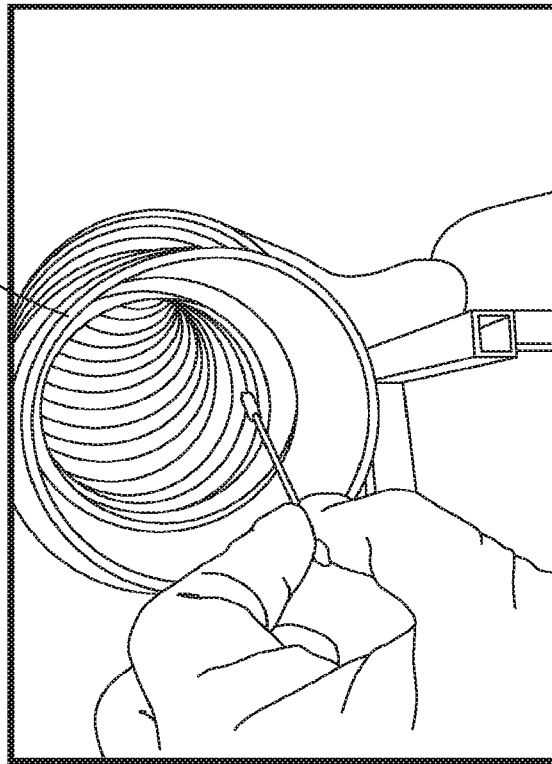
FIGS. 7A and 7B are photographs illustrating locations from which EAD samples are collected by swab for comparative analysis; (A) Horizontal exhaust plenum; (B) Exhaust plenum hose.
Figure 7A:
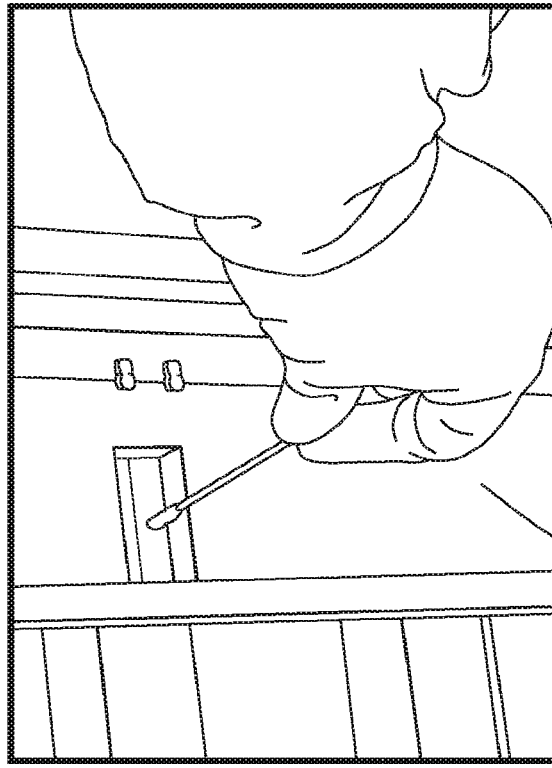

Additional dust samples were obtained from swabs of the IVR 302 for comparison with dust samples collected by the EAD collection media 322a, 322b, 322c. Dust swabs were collected at each horizontal plenum 314 and pooled (FIG. 7A), with evaluation every 3 months. Two dust swabs were also collected from an exhaust hose 700 connecting the vertical exhaust plenum 316 to the pre-HEPA filter assembly 310a (FIG. 7B), with evaluation every 3 months.

Sample Analysis

Nucleic Acid Isolation: Nucleic acid isolation is performed by magnetic isolation. For EAD captured by EAD collection media, the EAD collection media is positioned in a tube (e.g., the same tube in which the EAD collection media is transported), curved with the EAD facing inward. For dust collected by swabs, the swab(s) are transferred to a clean tube large enough to accommodate the number of swabs to be analyzed. A lysis solution is pipetted directly onto the EAD collection media or swab(s).

Respective tubes are subsequently subjected to vortex to thoroughly wash the EAD collection media or swab(s) with the lysis solution. Respective tubes are further centrifuged to spin the lysis solution down from the top of the first tube. A nucleic acid recovery control (NARC) is further added to respective tubes. The NARC allows for monitoring of any sample type and provides verification of recovery of nucleic acids present at in the lysis. Successful extraction (recovery of nucleic acid) as well as a successful reverse transcription reaction (RNA is transcribed to cDNA to detect RNA viruses by PCR) by performing a separate assay for the NARC template as part of the controls run during the PCR test analysis.

A selected amount of isopropanol is added to all sample wells, mixing while adding, followed by incubation at room temperature for at least 1 minute. A uniform suspension of mixing beads is added to each well containing a sample lysis and isopropanol.

Subsequently, the lysis samples and appropriate reagents are placed in a Kingfisher™ Magnetic Particle Processor 96 (Thermo Scientific™, Waltham, MA, USA). The Kingfisher™ uses permanent magnetic rods and disposable tip combs to move particles through the purification process.

Reverse Transcription: Reverse transcription of RNA into cDNA is further performed if the isolated nucleic acids contain RNA, as cDNA is required for RNA viruses (PCR requires DNA as a template). The reverse transcription is performed using a commercial kit. The kit reagents are prepared in reaction wells according to the manufacturer's instructions. For each sample to be tested that contains RNA, an appropriate volume of the sample is added to the corresponding reaction well. The wells are covered and centrifuged to ensure mixture of all components.

PCR Amplification: Samples evaluated for small panels of infectious agents are on a 96-well or 384-well real-time TaqMan PCR platform. Samples that are evaluated for large panels of infectious agents are first pre-amplified prior to amplification by real-time TaqMan PCR on an Open Array. The pre-amplification employs a concentration of primers (the same primers used for TaqMan assays discussed below). It is observed that, at full primer concentration, pre-amplification will permit an increase in copy number of about 3 Log 10. In general, primer concentration is limited to prevent any one template from dominating the reaction and preventing detection of templates present in smaller copy number (primer for large template agents is used up in the first couple cycles). The primer concentration is further limited in the pre-amplification for infectious agents that are known to always be present in large copy numbers.

Spike Control—A DNA spike control to monitor for PCR inhibition is added at the pre-amplification for panels evaluated on the Open Array. For 96 and 384-well formats, the spike is added as a separate assay during the PCR testing for all samples.

PCR Assays—PCR assays have been designed to incorporate sequences from public domains and unique sequences not available in the public domain.

100 copy templates were prepared by cloning target sequences into plasmid vectors and used as positive control templates. 1000 copy plasmids are also included for Open Array testing. Negative template wells are used for all formats. NARC and spike control mock samples processed alongside of field samples are evaluated to demonstrate function of these control templates and assays.

Assay Interpretation: Ct values obtained for samples are evaluated based on Ct value, but also general experience and observation to rule out cross-contamination. Valid CT values for determination of positive samples is based on experience and general knowledge of individual agents.

Test Results

Viruses

Table 1 compares testing results for samples obtained from four different sources: sentinel animals, EAD cage filters, EAD swabs, and EAD in-line filters. For sentinel animals, analysis is performed by serology, bacterial culture, and parasitology ("Traditional") and PCR. For EAD swabs, samples acquired from hose and plenum swabs, as discussed above, are analyzed by PCR. For EAD cage filters, dust samples are acquired without a sentinel animal being present within the cage ("no Sentinel") and with a sentinel animal present within the cage ("with Sentinel") and are analyzed by PCR. For EAD in-line filters, dust samples acquired from EAD collection media positioned within the IVR vertical exhaust plenum and adjacent the pre-HEPA filter are analyzed by PCR.

TABLE 1

VIRUS TESTING RESULTS

| | Sentinel | | EAD Cage Filter | | EAD Swab | | EAD In-Line Filter | |
| --- | --- | --- | --- | --- | --- | --- | --- | --- |
| Agent | Traditional | PCR | no Sentinel | with Sentinel | Hose Swab | Plenum Swab | Exhaust Filter | Pre-HEPA Filter |
| Adenovirus | 0 | 0 | 0 | 1 | 0 | 0 | 1 | 1 |
| Coronavirus | 1 | 0 | 0 | 4 | 1 | 1 | 1 | 1 |
| Mouse Parvoviruses | 4 | 1 | 0 | 4 | 1 | 1 | 1 | 1 |
| Theilovirus | 0 | 0 | 1 | 2 | 1 | 1 | 1 | 1 |
| Total % Positive | 31.3% | 6.3% | 6.3% | 68.8% | 75.0% | 75.0% | 100% | 100% |

From the results of Table 1, it may be observed that analysis of samples collected from sentinel animals yield the poorest indicator of viruses, detecting only 31% of viruses by traditional screening and about 6.3% by PCR. Analysis of samples collected from the cage-level EAD collection media exhibit mixed success, identifying only 6.3% of viruses when the sentinel was not present within the cage but approximately 68.8% of viruses when the sentinel was present. Analysis of samples collected from EAD swabs at the hose and plenum exhibit good accuracy, each detecting 75% of viruses. Analysis of samples collected in-line with exhaust air within the vertical exhaust plenum and adjacent the pre-HEPA filter exhibit the best accuracy, each detecting 100% of the viruses present.

Figure 8A:
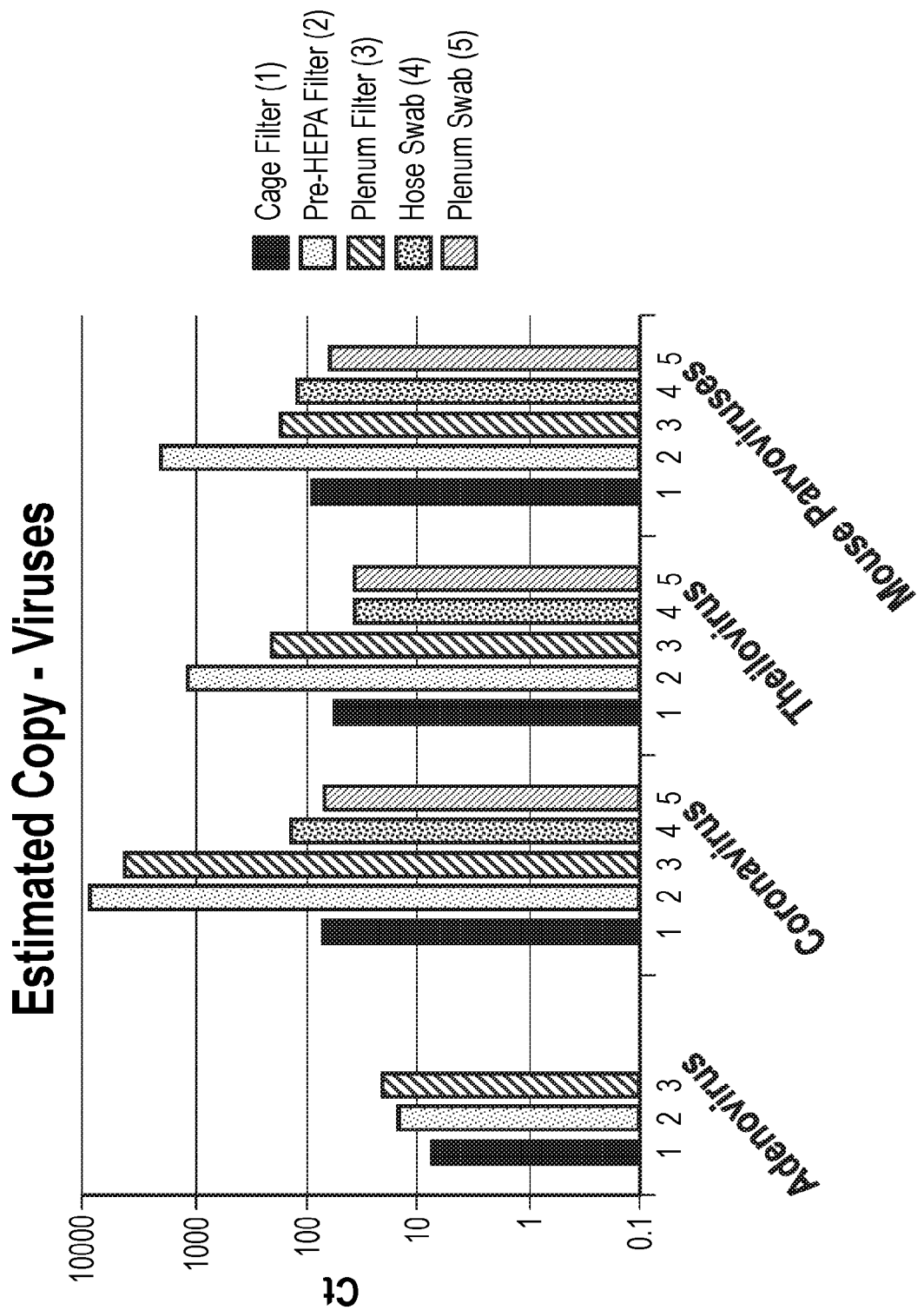
FIGS. 8A, 8B, 8C, and 8D are plots comparing estimated copy of pathogens detected by EAD collected from the EAD collection media and swabs.

Estimated copy of the above viruses, determined by real-time TaqMan PCR of dust samples collected from swabs and EAD collection media, is illustrated in FIG. 8A. As noted above, the Ct value is a relative measure of the concentration of a target. As elevated concentration increases likelihood of detection, higher values of Ct are preferred. It may be observed from FIG. 8A that for each virus, the EAD samples collected by the EAD collection media demonstrate Ct values comparable to or greater than swabbing.

Bacteria

Sample analysis for selected bacteria is illustrated in Table 2 below.

TABLE 2

BACTERIA TESTING RESULTS

| | Sentinel | | EAD Cage Filter | | EAD Swab | | EAD In-Line Filter | |
| | | | no | with | Hose | Plenum | Exhaust | Pre-HEPA |
| Agent | Traditional | PCR | Sentinel | Sentinel | Swab | Swab | Filter | Filter |
|---|---|---|---|---|---|---|---|---|
| Beta Strep Group B | 0 | 0 | 0 | 0 | 0 | 0 | 1 | 1 |
| H. ganmani | N/A | 0 | 0 | 2 | 0 | 0 | 1 | |
| H. hepaticus | N/A | 0 | 0 | 0 | 0 | 0 | 0 | |
| H. typhlonius | N/A | 0 | 0 | 3 | 1 | 1 | 1 | |
| Helicobacter | N/A | 0 | 2 | 4 | 1 | 1 | 1 | |
| M. pulmonis | 0 | 3 | 0 | 2 | 1 | 1 | 1 | 1 |
| P. mirabilis | 0 | 0 | 2 | 3 | 1 | 0 | 0 | 0 |
| P. multocida | 0 | 0 | 0 | 1 | 0 | 0 | 1 | 1 |
| P. pneumotropica | 0 | 3 | 1 | 4 | 1 | 1 | 1 | |
| S. aureus | 0 | 0 | 0 | 0 | 0 | 0 | 1 | 1 |
| Total % Positive | 0% | 15.0% | 12.5% | 47.5% | 50.0% | 40% | 80% | 40% |

From Table 2, it may be observed that analysis of samples collected from sentinel animals yield the poorest indicator of bacteria, detecting none of bacteria by traditional screening and 15% by PCR. Analysis of samples collected by the cage-level EAD collection media exhibit mixed success, identifying only 12.5% of bacteria when the sentinel is not present within the cage but approximately 47.5% of bacteria when the sentinel is present. Analysis of samples collected from EAD swabs at the hose and plenum detect 50% and 40% of bacteria present. Analysis of samples collected by EAD collection media in-line with exhaust air within the vertical exhaust plenum exhibit the best accuracy, detecting 80% of the bacteria present. Analysis of samples collected in-line with the exhaust airflow and adjacent the pre-HEPA filter detect 40% of the bacteria present.

Figure 8B:
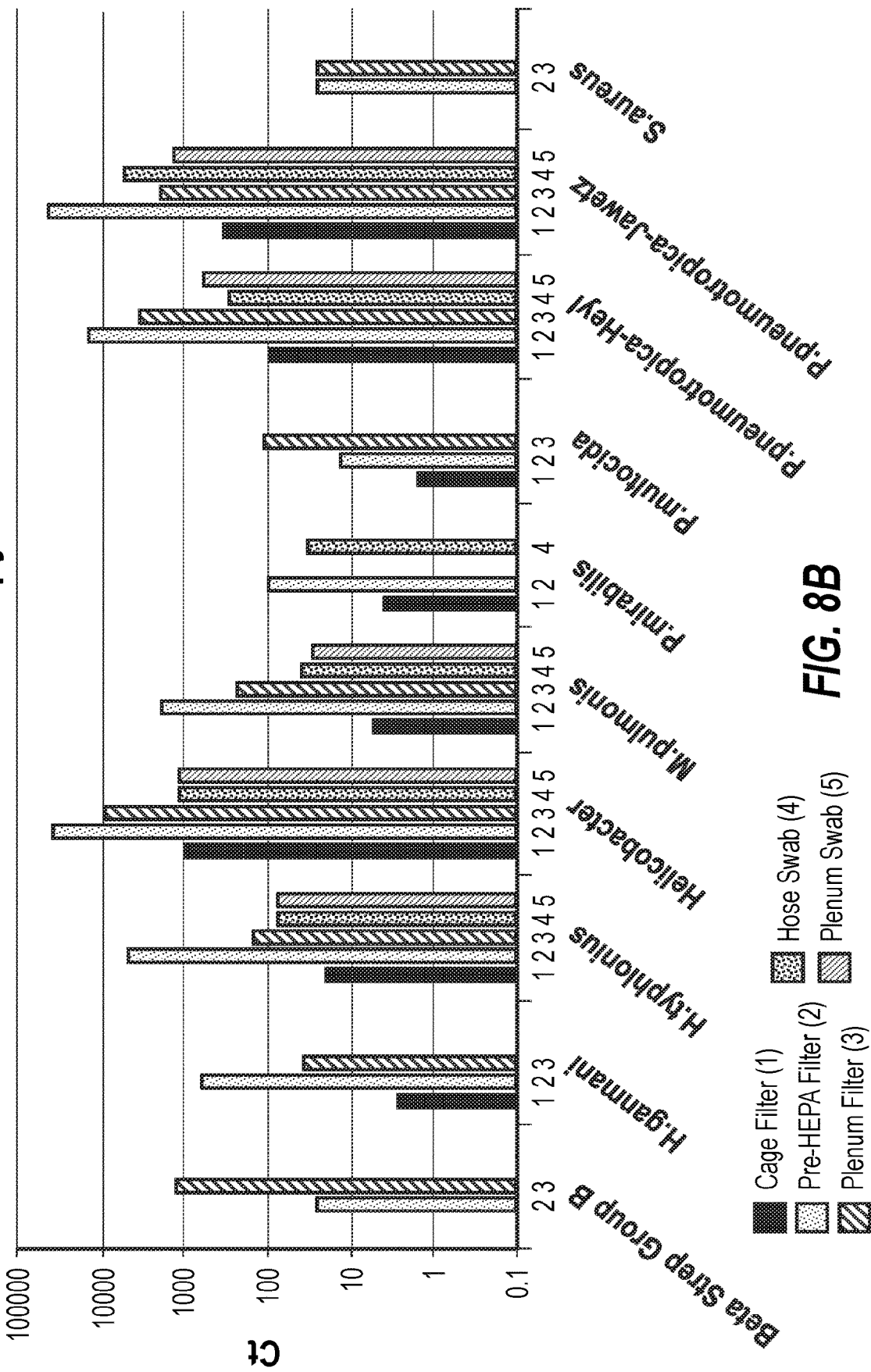

Estimated copy of the above bacteria is determined by real-time TaqMan PCR of dust samples collected from swabs and EAD collection media is illustrated in FIG. 8B. As noted above, the Ct value is a relative measure of the concentration of a target. As elevated concentration increases likelihood of detection, higher values of Ct are preferred. It may be observed from FIG. 8B that for each bacteria, the EAD samples collected by the EAD collection media demonstrate Ct values roughly comparable to or greater than swabbing.

Protozoa

Analysis of each sample for selected protozoa is illustrated in Table 3 below.

TABLE 3

PROTOZOA TESTING RESULTS

| | Sentinel | | EAD Cage Filter | | EAD Swab | | EAD In-Line Filter | |
| --- | --- | --- | --- | --- | --- | --- | --- | --- |
| Agent | Traditional | PCR | no Sentinel | with Sentinel | Hose Swab | Plenum Swab | Exhaust Filter | Pre-HEPA Filter |
| *Cryptosporidium* | 0 | 0 | 0 | 2 | 1 | 1 | 1 | 1 |
| *Entamoeba* | 2 | 2 | 0 | 4 | 1 | 1 | 1 | 1 |
| *Giardia* | 0 | 0 | 0 | 1 | 0 | 0 | 1 | 1 |
| *Spironucleus muris* | 0 | 0 | 0 | 2 | 1 | 0 | 1 | 1 |
| *Tritichomonas* | 0 | 0 | 4 | 4 | 1 | 1 | 1 | 1 |
| Total % Positive | 31.3% | 10% | 20% | 65% | 80% | 60% | 100% | 100% |

From Table 3, it may be observed that analysis of samples collected from sentinel animals yield relatively poor indication of protozoa, detecting only 31.3% of protozoa by traditional screening and about 10% by PCR. Analysis of samples collected from the cage-level EAD collection media exhibit mixed success, identifying only 20% of protozoa when the sentinel was not present within the cage but approximately 65% of protozoa when the sentinel was present. Analysis of samples collected from EAD swabs at the hose and plenum exhibit good accuracy, detecting 80% of protozoa by hose swab and 60% of protozoa by plenum swab. Analysis of samples collected by EAD collection media in-line with exhaust airflow exhibit the best accuracy, each detecting 100% of the protozoa present.

Figure 8C:
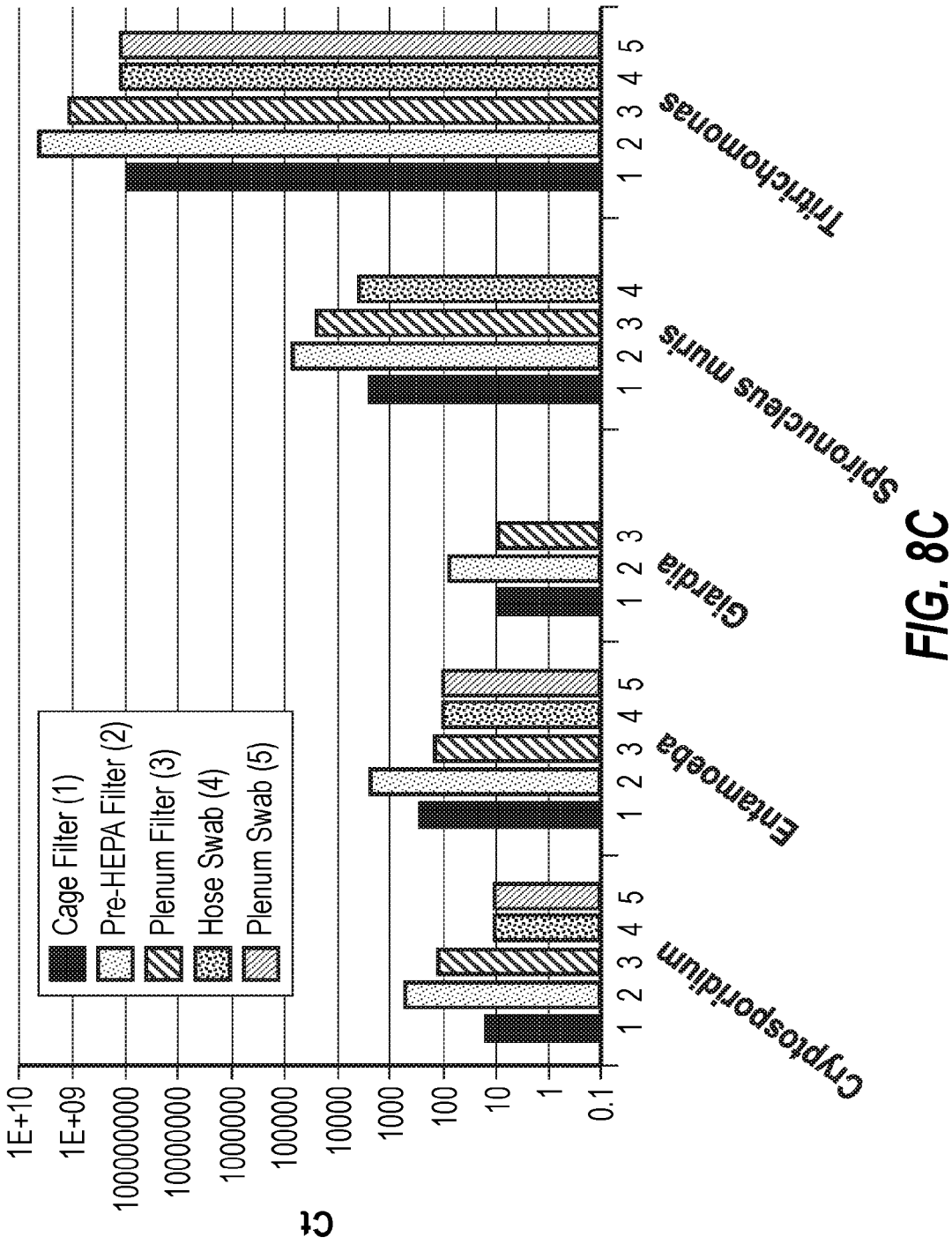

Estimated copy of the above protozoa determined by real-time TaqMan PCR of collected EAD samples is illustrated in FIG. 8C. As noted above, the Ct value is a relative measure of the concentration of a target. As elevated concentration increases likelihood of detection, higher values of Ct are preferred. It may be observed from FIG. 8C that for each protozoa, the EAD samples collected by the EAD collection media demonstrated Ct values comparable to or greater than swabbing.

Metazoan Parasites

Analysis of each sample for selected parasites is illustrated in Table 4 below.

present. Analysis of samples collected by the EAD collection media in-line with the exhaust airflow adjacent the pre-HEPA filter detected 50% of the parasites present.

Figure 8D:
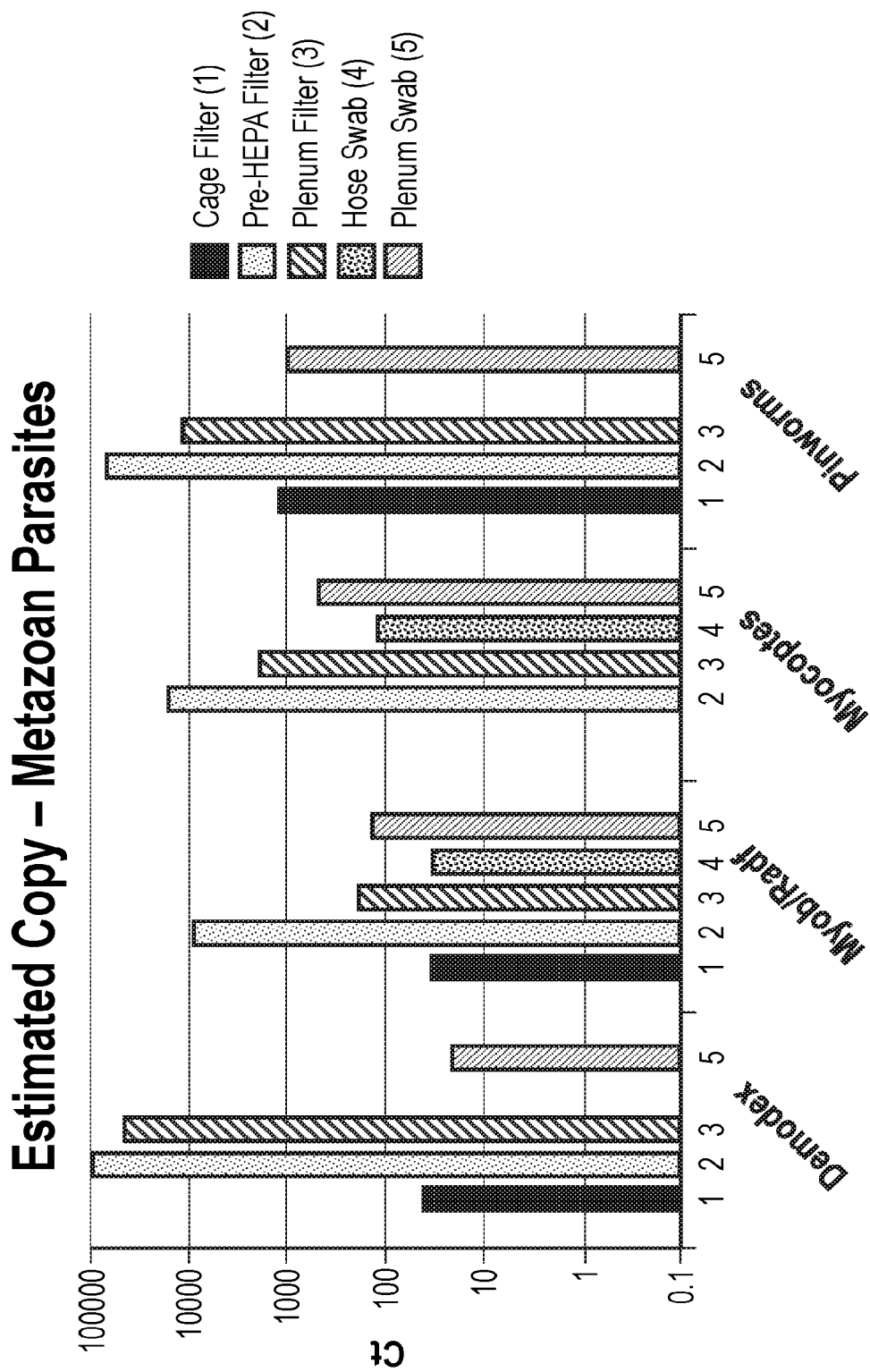

Estimated copy of the above parasites determined by real-time TaqMan PCR of collected EAD samples is illustrated in FIG. 8D. As noted above, the Ct value is a relative measure of the concentration of a target. As elevated concentration increases likelihood of detection, higher values of Ct are preferred. It may be observed from FIG. 8D that for each parasite, the EAD samples collected by the EAD collection media demonstrated Ct values comparable to or greater than swabbing.

These testing results indicate that PCR analysis of EAD samples collected by EAD collection media in-line with exhaust airflow according to embodiments of the instant disclosure detect pathogens at a level comparable to or greater than traditional sentinels or EAD swabs. The concentration of sampled pathogens is also comparable to or greater than traditional sentinels or EAD swabs.

Significantly, EAD collected by EAD collection media at the cage level was a relatively poor indicator of pathogens when a sentinel animal is not present in the cage. However, the accuracy of these samples increased significantly when a sentinel animal is present within the cage. It is believed that this difference is the result of dust agitation provided by the moving animal.

TABLE 4

PARASITE TEST RESULTS

| | Sentinel | | Sentinel Cage Filter | | EAD Swab | | EAD In-Line | |
| --- | --- | --- | --- | --- | --- | --- | --- | --- |
| Agent | Traditional | PCR | no Sentinel | with Sentinel | Hose Swab | Plenum Swab | Exhaust Filter | Pre-HEPA Filter |
| *Demodex* | 0 | 0 | 0 | 1 | 0 | 1 | 1 | 1 |
| *Myobia/Radforia* | 0 | 1 | 0 | 2 | 1 | 1 | 1 | 0 |
| *Myocoptes* | 0 | 0 | 0 | 0 | 1 | 1 | 1 | 0 |
| Pinworms | 0 | 0 | 0 | 4 | 0 | 1 | 1 | 1 |
| Total % Positive | 0% | 6.3% | 0% | 43.8% | 50% | 100% | 100% | 50% |

Figure 9:
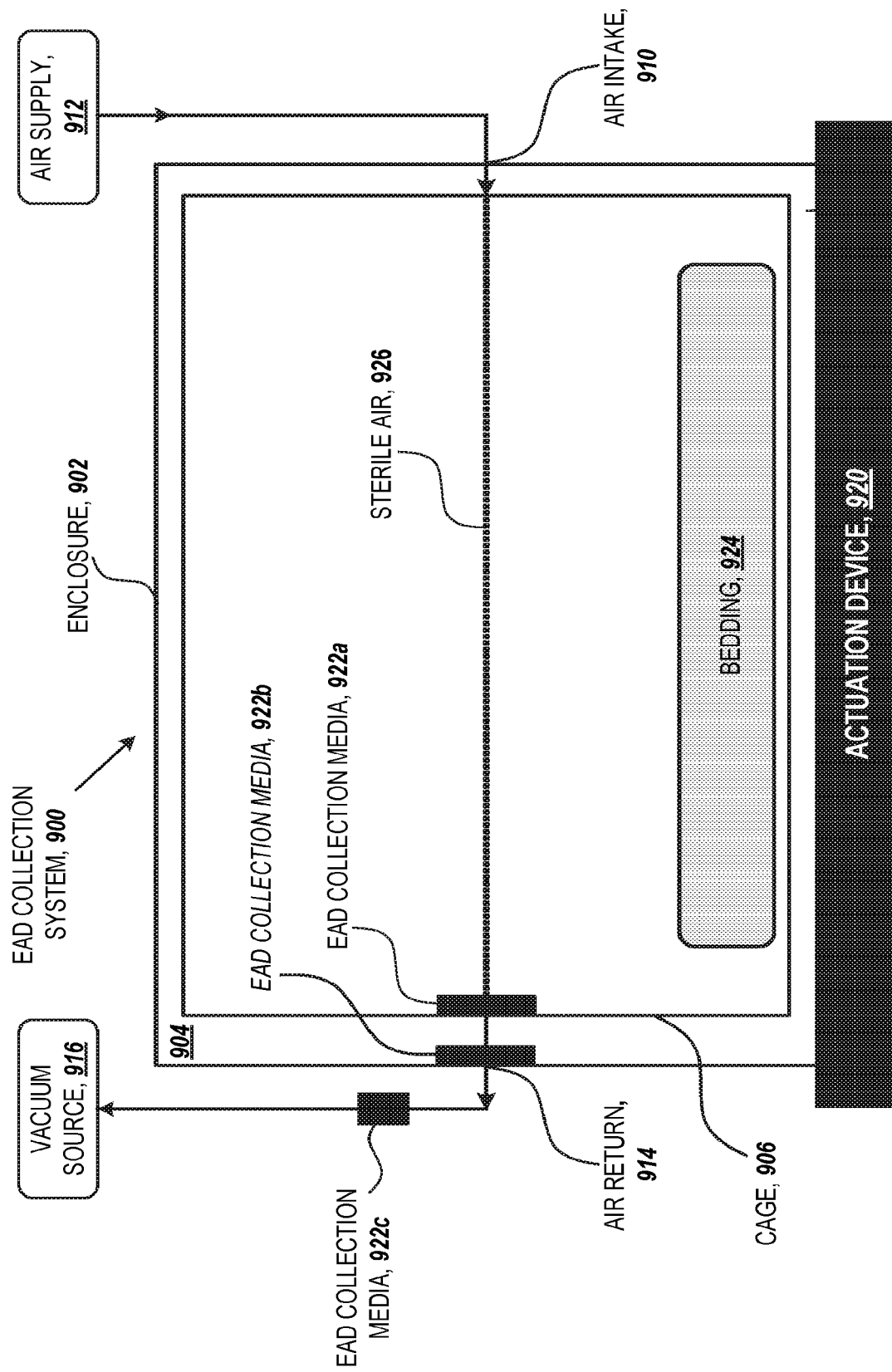
FIG. 9 is a schematic illustration of an embodiment of an EAD collection system configured for operation independent of an individually ventilated cage rack.

It may be observed from Table 4 that analysis of samples collected from sentinel animal yield relatively poor indication of parasites, detecting none of the parasites by traditional screening and about 6.3% by PCR. Analysis of samples collected from the cage-level EAD collection media exhibit mixed success, identifying none of the parasites when the sentinel is not present within the cage but approximately 43.8% of parasites when the sentinel is present. Analysis of samples collected by EAD collection media in-line with the exhaust airflow within the exhaust plenum exhibit excellent accuracy, detecting 100% of the parasites present To explore the anticipated benefits of dust agitation, without requiring the use of a sentinel animal, an EAD collection system 900, illustrated in FIG. 9, is further evaluated. The system 900 includes a reversibly sealable enclosure 902 including a chamber 904 adapted to receive an animal cage 906, an air intake 910 coupleable with an air supply 912, and an air return 914 coupleable with a vacuum source 916. The system 900 further includes an actuation device 920 and a plurality of EAD collection media 922 (e.g., 922a, 922b, 922c).

The actuation device 920 is in mechanical communication with the enclosure 902 and operable to agitate the contents of a cage 906 positioned within the chamber 904. The actuation device 920 may be configured to move the enclosure 902 horizontally, vertically, and/or rotationally, alone or in any combination, in order to release dust particles from bedding 924 positioned within the cage 906. In further embodiments, the actuation device 920 may be an ultrasonic device.

The EAD collection media 922 are suitable for capturing EAD transported by a flow of sterile air 926 directed through the enclosure 902. The EAD collection media 922 may EAD collection media 224, as discussed above. In an embodiment, one or more EAD collection media 922a is positioned within the cage 906 (e.g., on a wall of the cage 906 or suspended therein). In another embodiment, one or more EAD collection media 922b is positioned outside of the cage 906 and within the enclosure 902 (e.g., on a wall of the enclosure 902 or suspended within the chamber 904). In further embodiments, one or more EAD collection media 922c is positioned outside of the enclosure 902 (e.g., within an airflow pathway in fluid communication with the vacuum source 916).

EAD collected using the system 900 may be further analyzed for detection of pathogens according to the method 100, where the collection operation 102 is performed as discussed above with respect to the system 900. Operations 104-114 of method 100 are otherwise unchanged.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. Nothing herein is to be construed as an admission that the invention is not entitled to antedate such disclosure by virtue of prior invention.

Every formulation or combination of components described or exemplified herein can be used to practice the invention, unless otherwise stated.

Whenever a range is given in the specification, for example, a temperature range, a time range, or a composition or concentration range, all intermediate ranges and sub-ranges, as well as all individual values included in the ranges given are intended to be included in the disclosure. As used herein, ranges specifically include the values provided as endpoint values of the range. For example, a range of 1 to 100 specifically includes the end point values of 1 and 100. It will be understood that any sub-ranges or individual values in a range or sub-range that are included in the description herein can be excluded from the claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A system for providing a test sample comprising environmental air dust captured from an airflow path within an individually vented cage rack (IVR) comprising: at least one enclosure in the IVR configured for housing one or more non-sentinel animals; an actuation device in direct contact with or within the at least one enclosure for agitating the at least one enclosure and/or soiled bedding therein for releasing the environmental air dust therefrom; an IVR air supply in fluid communication with a source of sterile air; an IVR vacuum source; an IVR air intake in fluid communication with the IVP air supply; an IVP air return in fluid communication with the IVP vacuum source; wherein the airflow path flows intermediate the IVP air intake and the IVP air return and passing through the at least one enclosure; and at least one collection media disposed within the at least one enclosure for capturing the from the airflow path as the test sample, wherein the at least one collection media impinges at least a portion of the airflow path, and wherein the at least one collection media is positioned to capture EAD while not substantially interfering with airflow through the at least one enclosure.

2. The system of claim 1, wherein the at least one collection media is removable from the IVR.

3. The system of claim 1, wherein the at least one collection media is a graded filter.

4. The system of claim 1, wherein the at least one collection media comprises a filter selected from the group consisting of a mechanical filter, a chemical filter, a wet scrubber, and an electrostatic filter.

5. The system of claim 1, wherein the actuation device is configured to move the at least one enclosure at least one of horizontally, vertically and rotationally.

6. The system of claim 5, wherein the actuation device is configured to reversibly move the at least one enclosure at least one of horizontally, vertically and rotationally.

7. The system of claim 1, wherein the actuation device is an ultrasonic device.

8. The system of claim 1, wherein the test sample comprises environmental air dust captured from the airflow path over a time period of at least two weeks.

9. The system of claim 1, wherein the IVR further comprises at least one cage for housing a test animal.

10. The system of claim 9, wherein the test sample further comprises at least one of fecal pellets obtained from the test animal, biological material obtained from an oral swab of the test animal, biological material obtained from a body swab of the test animal, and tissue from the test animal.

11. The system of claim 10, wherein the one or more pathogens is selected from the group consisting of: *Staphylococcus* spp., *Pasteurella* spp., *Proteus* spp., *Klebsiella* spp., *Giardia* spp., *Cryptosporidium* spp., *Entamoeba* spp., *Spironucleus* spp., Murine norovirus, *Pseudomonas* spp., and beta-hemolytic *Streptococcus* spp.

12. The system of claim 9, wherein the enclosure comprises at least one cage, and the at least one collection media is at least one of disposed on an interior wall of the at least one cage and suspended within the at least one cage.

13. The system of claim 9, wherein the at least one collection media is at least one of disposed on a wall of the at least one enclosure and suspended within the at least one enclosure-outside the at least one cage.

14. The system of claim 13, wherein the enclosure comprises at least one cage, and the at least one collection media is at least one of on top of the at least one cage, adjacent to the at least one cage, and on an exterior side wall of the at least one cage.

15. The system of claim 1, wherein the IVR does not comprise a cage housing a sentinel animal.

16. The system of claim 1, wherein the IVR further comprises an exhaust plenum in the airflow path intermediate the IVR air intake and the IVR air return and wherein a second collection media is disposed within the exhaust plenum for capturing the environmental air dust from the airflow path.

17. The system of claim 16, wherein a surface of the second collection media is oriented at an acute angle with respect to the airflow path within the exhaust plenum.

18. The system of claim 17, wherein the angle of the second collection media during capture of the test sample is selected within the range from 15° to 25° with respect to the direction of the airflow path within the exhaust plenum.

19. The system of claim 1, wherein pressure within the at least one enclosure varies by less than or equal to +10% due to reduced airflow caused by the second collection media in the IVR airflow path as compared to the pressure within the at least one enclosure absent the EAD collection media.

20. A system for providing a test sample comprising environmental air dust (EAD) captured from an individually vented cage rack (IVR) airflow path within an IVR comprising: an IVR air supply in fluid communication with a source of sterile air; an IVR vacuum source; at least one enclosure in the IVR comprising; an animal cage for housing one or more non-sentinel animals, each of the at least one enclosure comprising a cape-level air intake in fluid communication with the IVR air supply and a cage-level air return in fluid communication with the IVR vacuum source; an actuation device in direct contact with or within the at least one enclosure for agitating the at least one enclosure and/or soiled bedding within the animal cage for releasing the environmental air dust therefrom; at least one cage-level airflow path through the at least one enclosure in the IVR, the cage-level airflow path being intermediate the cage-level air intake and the cage-level air return; and at least one collection media disposed within the IVR for capturing the EAD from the cage-level airflow path as the test sample, wherein the at least one collection media impinges at least a portion of the cage-level airflow path, and wherein the at least one collection media is positioned to capture EAD while not substantially interfering with airflow through the IVR, and wherein the IVR airflow path comprises the cage-level airflow path.

21. The system of claim 20, wherein the at least one collection media is removable from the IVR.

22. The system of claim 20, wherein the at least one collection media is a graded filter.

23. The system of claim 20, wherein the at least one collection media comprises a filter selected from the group consisting of a mechanical filter, a chemical filter, a wet scrubber, and an electrostatic filter.

24. The system of claim 20, wherein the actuation device is configured to move the at least one enclosure at least one of horizontally, vertically and rotationally.

25. The system of claim 24, wherein the actuation device is configured to reversibly move the at least one enclosure at least one of horizontally, vertically and rotationally.

26. The system of claim 20, wherein the actuation device is an ultrasonic device.

27. The system of claim 20, wherein the test sample comprises environmental air dust captured from the cage-level airflow path over a time period of at least two weeks.

28. The system of claim 20, wherein the animal cage comprises a test animal, and the test sample further comprises at least one of fecal pellets obtained from the test animal, biological material obtained from an oral swab of the test animal, biological material obtained from a body swab of the test animal, and tissue from the test animal.

29. The system of claim 28, wherein the one or more pathogens is selected from the group consisting of: *Staphylococcus* spp., *Pasteurella* spp., *Proteus* spp., *Klebsiella* spp., *Giardia* spp., *Cryptosporidium* spp., *Entamoeba* spp., *Spironucleus* spp., Murine norovirus, *Pseudomonas* spp., and beta-hemolytic *Streptococcus* spp.

30. The system of claim 20, wherein the at least one collection media is at least one of disposed on an interior wall of the cage and suspended within the cage.

31. The system of claim 20, wherein the at least one collection media is disposed outside the cage.

32. The system of claim 20, wherein the at least one collection media is at least one of on top of the cage, adjacent to the cage, on an exterior side wall of the cage, on a wall of the at least one enclosure, and suspended within the at least one enclosure.

33. The system of claim 20, wherein the IVR does not comprise a cage housing a sentinel animal.

34. The system of claim 20, wherein the IVR further comprises an exhaust plenum in the IVR airflow path after the at least one enclosure and wherein [the] a second collection media is disposed within the exhaust plenum for capturing the environmental air dust from the IVR airflow path.

35. The system of claim 34, wherein a surface of the second collection media is oriented at an acute angle with respect to the IVR airflow path within the exhaust plenum.

36. The system of claim 35, wherein the angle of the second collection media during capture of the test sample is selected within the range from 15° to 25° with respect to the direction of the IVR airflow path within the exhaust plenum.

37. The system of claim 20, wherein pressure within the at least one enclosure varies by less than or equal to +10% due to reduced airflow caused by the second collection media in the IVR airflow path as compared to the pressure within the at least one enclosure absent the EAD collection media.

* * * * *